US012533481B2

(12) United States Patent
Salvino

(10) Patent No.: US 12,533,481 B2
(45) Date of Patent: Jan. 27, 2026

(54) NASAL CANNULA SHIELD

(71) Applicant: Chris Salvino, Scottsdale, AZ (US)

(72) Inventor: Chris Salvino, Scottsdale, AZ (US)

(73) Assignee: SharpMed, LLC., Scottsdale, AZ (US)

( * ) Notice: Subject to any disclaimer, the term of this patent is extended or adjusted under 35 U.S.C. 154(b) by 0 days.

(21) Appl. No.: 19/090,306

(22) Filed: Mar. 25, 2025

(65) Prior Publication Data

US 2025/0312549 A1 Oct. 9, 2025

Related U.S. Application Data

(60) Provisional application No. 63/575,781, filed on Apr. 7, 2024.

(51) Int. Cl.
*A61M 16/06* (2006.01)

(52) U.S. Cl.
CPC ................................ *A61M 16/0672* (2014.02)

(58) Field of Classification Search
CPC .......... A61M 16/0605; A61M 16/0611; A61M 16/0666–0677; A61M 15/08; A61M 15/085; A61F 5/08; A62B 23/06
See application file for complete search history.

(56) References Cited

U.S. PATENT DOCUMENTS 4,156,426 A * 5/1979 Gold ................. A61M 16/0666 128/207.18
4,774,946 A * 10/1988 Ackerman ........ A61M 16/0633 128/207.18
4,915,105 A * 4/1990 Lee ........................ A62B 18/00 128/205.27
4,919,128 A * 4/1990 Kopala ............. A61M 16/0666 128/207.18
5,113,857 A * 5/1992 Dickerman ......... A61M 15/085 128/207.18
10,695,517 B2 6/2020 Lei
11,364,358 B2 6/2022 Cortez et al.
2012/0204870 A1* 8/2012 McAuley .......... A61M 16/0622 128/207.18
2012/0318274 A1* 12/2012 Ho .................... A61M 16/0683 128/207.18
2015/0068530 A1* 3/2015 Apolito ............. A61M 16/0683 128/207.18
2015/0136139 A1* 5/2015 Franzen ............ A61M 16/0605 128/205.25
2017/0143926 A1* 5/2017 Allum ............... A61M 16/0672
2021/0353885 A1 11/2021 Landis et al.
2022/0054786 A1* 2/2022 Huss ................. A61M 16/1045

* cited by examiner

*Primary Examiner* — Valerie L Woodward
(74) *Attorney, Agent, or Firm* — Kenneth Altshuler

(57) ABSTRACT

Described herein are embodiments directed to embodiments of a nasal cannula assembly that generally comprises a pair of hollow cannula posts that extend from a center cylinder. Oxygen is pressurized to flow into the center cylinder and out through outlet ports in the terminating ends of the cannula posts. A pair of nasal shields are fixedly attached to the cannula posts. The nasal shields have an outward facing convex curved outer surface that can be flush with the post terminating ends. The pair of nasal shields each have a nasal shield aperture that aligns with the outlet ports. The nasal shields are configured to essentially cover a pair of human nostrils.

20 Claims, 27 Drawing Sheets

NASAL CANNULA SHIELD

CROSS-REFERENCE TO RELATED APPLICATIONS

This application claims priority to and the benefit of U.S. Provisional Patent Application No. 63/575,781 entitled: Nasal Cannula Shield, filed on Apr. 7, 2024.

FIELD OF THE INVENTION

The present embodiments are directed to low oxygen leaking nasal cannulas.

DESCRIPTION OF RELATED ART

A nasal cannula is a medical device used to deliver supplemental oxygen to patients who require respiratory support. It comprises a flexible tube with two prongs that are inserted into the nostrils, through which oxygen flows from a connected oxygen source. Nasal cannulas are commonly used in hospital settings, emergency care, and at home for patients with chronic respiratory conditions such as COPD (chronic obstructive pulmonary disease), asthma, or pneumonia. The device allows patients to breathe normally while receiving the oxygen they need, and it is often preferred over other methods, like masks, due to its comfort and ease of use.

One of the advantages of using a nasal cannula is its non-intrusive design, which allows patients to talk, eat, and move around more freely compared to other oxygen delivery systems. The simplicity and flexibility of the nasal cannula make it an essential tool for long-term oxygen therapy in both clinical and home care settings.

It is to improvements related to nasal cannulas that embodiments of the present invention are directed.

SUMMARY OF THE INVENTION

The present embodiments generally relate to nasal cannulas that have low oxygen leakage.

One inventive aspect of the present invention is directed to a nasal cannula assembly, that generally comprises a pair of cannula posts extending from a center cylinder. Each of the cannula posts defines an outlet port at a post terminating end. A first intake tube sleeve extends from a first center cylinder end of the center cylinder and a second intake tube sleeve extends from a second center cylinder end of the center cylinder. Each of the pair of nasal shields having a convex curved outer surface that is flush with the post terminating ends. A pair of nasal shields are fixedly attached to the cannula posts at the post terminating ends. The pair of nasal shields each have a nasal shield aperture that aligns with the outlet ports. The pair of nasal shields are configured to essentially cover a pair of human nostrils.

Another embodiment of the present invention envisions a nasal cannula that generally comprises a center cylinder defined between a first cylinder end and a second cylinder end with an oxygen input port at the first cylinder end, that is only one input port to receive the oxygen. A pair of cannula posts extend to post terminating ends from the center cylinder between the first and the second cylinder ends, wherein each of the post terminating ends comprising an outlet port. A pair of nasal shields are each attached to one of the cannula posts. Each of the nasal shields have a convex curved outer surface with a shield aperture extending therethrough. Each of the shield apertures accommodate fluid communication between the oxygen input port and the outlet ports.

Yet another embodiment of the present invention envisions a flush shield nasal cannula that comprises a center cylinder defined between a first cylinder end and a second cylinder end, wherein the first cylinder end is configured to receive oxygen. The flush shield nasal cannula further comprises a pair of cannula posts extending from the center cylinder to outlet ports. A pair of asymmetrically shaped nasal shields each attached to one of the cannula posts, wherein each of the nasal shields comprises a convex curved outer surface with a shield aperture extending therethrough. Each of the shield apertures accommodates fluid communication between the oxygen input port and the outlet ports, wherein each of the convex curved outer surface is configured to substantially block a wearer's nostril from an exterior environment, that is not by way of through the nasal cannula. Optionally, it is further envisioned that each of the outlet ports is defined by a distal rim that does not extend beyond the convex curved outer surface.

BRIEF DESCRIPTION OF THE DRAWINGS

FIG. 12B is an exploded offset angle view line drawing of the nose cup cannula embodiment depicted in FIG. 12A;

DETAILED DESCRIPTION

Figure 1A:
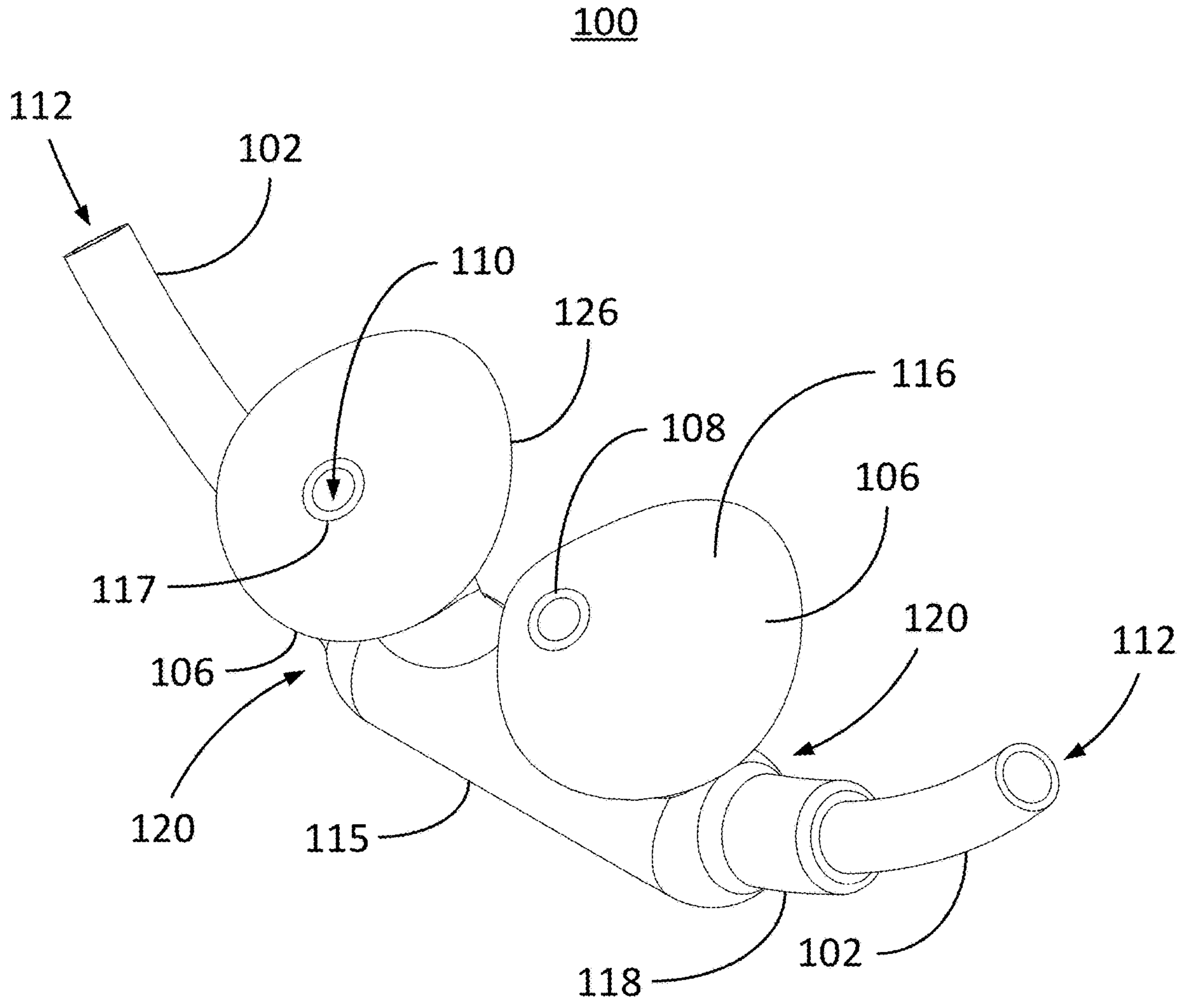
FIGS. 1A and 1B are line drawings of a low leakage nasal cannula embodiment consistent with embodiments of the present invention.

Initially, this disclosure is by way of example only, not by limitation. Thus, although the instrumentalities described herein are for the convenience of explanation, shown and described with respect to exemplary embodiments, it will be appreciated that the principles herein may be applied equally in other similar configurations involving similar uses of the technology put forth in the field of the invention. The phrases "in one embodiment", "according to one embodiment", and the like, generally mean the particular feature, structure, or characteristic following the phrase, is included in at least one embodiment of the present invention and may be included in more than one embodiment of the present invention. Importantly, such phases do not necessarily refer to the same embodiment. If the specification states a component or feature "may", "can", "could", or "might" be included or have a characteristic, that particular component or feature is not required to be included or have the characteristic. As used herein, the terms "having", "have", "including" and "include" are considered open language and are synonymous with the term "comprising". Furthermore, as used herein, the term "essentially" is meant to stress that a characteristic of something is to be interpreted within acceptable tolerance margins known to those skilled in the art in keeping with typical normal world tolerance, which is analogous with "more or less." For example, essentially flat, essentially straight, essentially on time, etc., all indicate that these characteristics are not expected or even capable of being perfect within the sense of their limits. Accordingly, if there is no specific +/− value assigned to "essentially", then it is to be assumed that "essentially" has a default meaning to be within +/−2.5% of exact. The term "connected to" as used herein is to be interpreted as a first element physically linked or attached to a second element and not as a "means for attaching" as in a "means plus function". In fact, unless a term expressly uses "means for" followed by the gerund form of a verb, that term shall not be interpreted under 35 U.S.C. § 112(f). In what follows, similar or identical structures may be identified using identical callouts.

With respect to the drawings, it is noted that the figures are not necessarily drawn to scale and are diagrammatic in nature to illustrate features of interest. Descriptive terminology such as, for example, upper/lower, top/bottom, horizontal/vertical, left/right and the like, may be adopted with respect to the various views or conventions provided in the figures as generally understood by an onlooker for purposes of enhancing the reader's understanding and is in no way intended to be limiting. All embodiments described herein are submitted to be operational irrespective of any overall physical orientation unless specifically described otherwise, such as elements that rely on gravity to operate, for example.

Described herein are embodiments directed to embodiments of a nasal cannula assembly that generally comprises a pair of hollow cannula posts that extend from a center cylinder. Oxygen is pressurized to flow into the center cylinder and out through outlet ports in the terminating ends of the cannula posts. A pair of nasal shields are fixedly attached to the cannula posts. The nasal shields have an outward facing convex curved outer surface that can be flush with the post terminating ends. The pair of nasal shields each have a nasal shield aperture that aligns with the outlet ports. The nasal shields are configured to essentially cover a pair of human nostrils.

Figure 14:
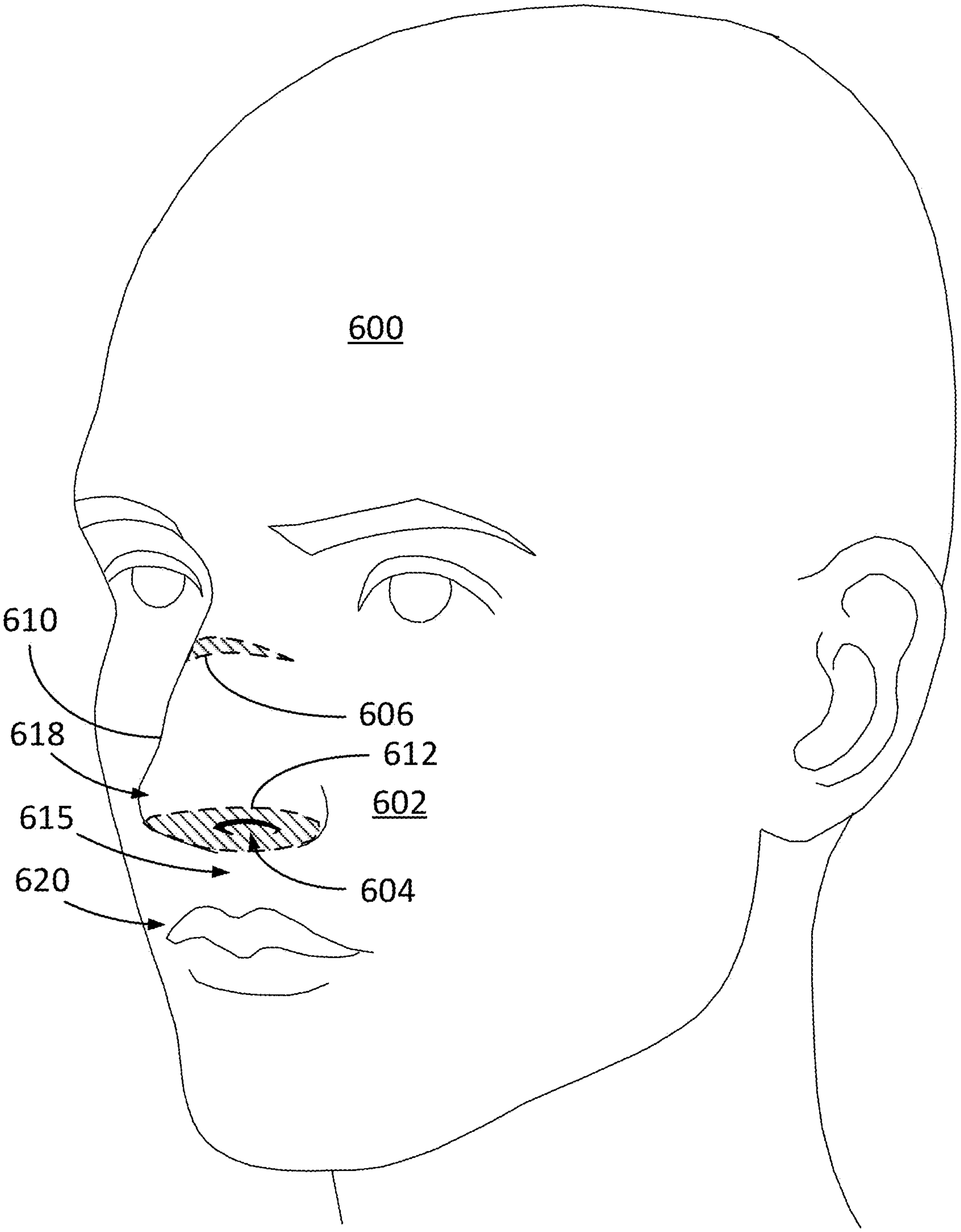
FIG. 14 is a line drawing depicting a person's face that is used to reference anatomy for embodiments of the present invention.

The description references parts of a human face, which is depicted in FIG. 14. FIG. 14 is diagrammatic line drawing of a person's face referencing the relative position of the parts of a person's face. Accordingly, throughout the figures, when facial callouts are referenced, they are done so in view of FIG. 14.

Figure 1B:
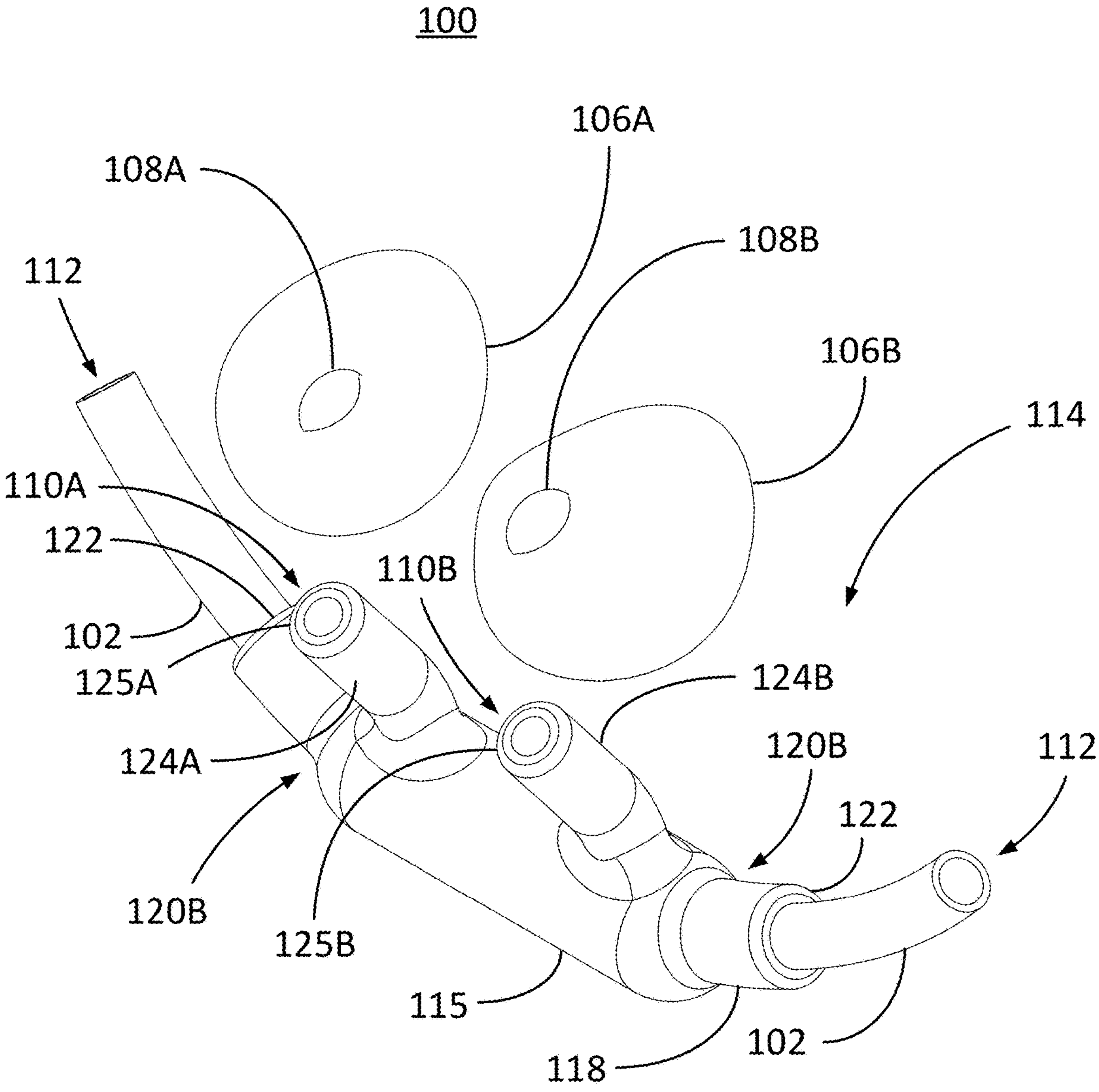
Figure 2A:
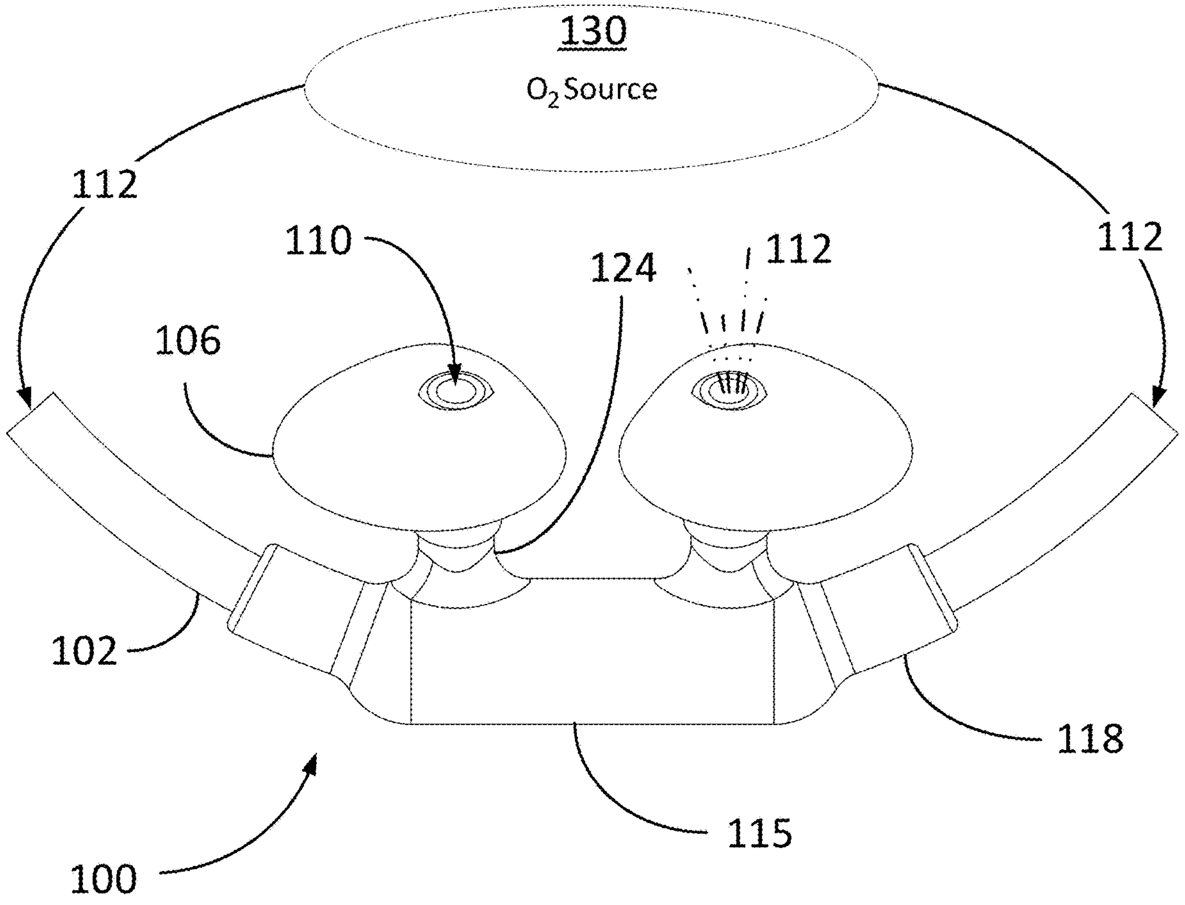
FIG. 2A is a line drawing illustratively depicting a front view of the cannula embodiment connected to an oxygen source consistent with embodiments of the present invention.

FIGS. 1A and 1B are line drawings of a low leakage nasal cannula embodiment consistent with embodiments of the present invention. FIG. 1A is a three-quarter view line drawing of a low leakage flush shield nasal cannula embodiment 100, or simply "cannula 100", which comprises flush nasal shields 116. The flush nasal shields 106 are so called because the face/surface of the shields 116 are essentially flush with the distal ends of the 124 cannula posts 124, where the nasal shield apertures 108 are located. The cannula 100 generally comprises two nasal cannula shields 106 that are each attached to the ends 125 of a corresponding nasal cannula post 124. The two nasal cannula shields 106 are configured to help prevent oxygen leakage from the wearer's nostrils 604. As shown in FIGS. 1A and 1B, the cannula 100 generally comprises a pair of cannula posts 124 extending orthogonally from a center cylinder 115. Each of the cannula posts 124 define an outlet port 110 at a post terminating end 125. Oxygen 112, from an oxygen source 130, as shown in FIG. 2A, flows through the oxygen tubes 102, into the cannula 100 and out through the outlet ports 110. The oxygen tubes 102 connect to intake tube sleeves 118 on either end 120 of the center cylinder 115.

The pair of nasal shields 106 are generally defined by outward facing convex/rounded surfaces 116 that interface nostrils 604 (not shown). Each of the nasal shields 106 when attached to the corresponding cannula posts 124 resemble the shape of a mushroom. In certain embodiments, the nasal shields 106 are a soft pliable polymer, such as rubber or latex, for example. The cannula posts 124, on the other hand, can be a relatively stiff polymer, such as PVC or some other suitable material that is rigid enough to hold its shape. Each convex curved surface 116 of the nasal shields 106 comprises a shield periphery 126 that extends beyond the opening of a nostril 604 thereby blocking the nostril 604 to ensure oxygen flow meets the needs of the patient 600. In this arrangement, at least a portion of the convex curved surface 116 penetrates the distal portion of the nostril 604 with the nasal shield aperture 108 located at the convex curved surface apex 117, which pours or otherwise dispenses oxygen 112 into the wearer's sinuses. As shown, in the present embodiment, the shape of a nasal shield 106 is not symmetrical meaning that the left side of the convex curved surface 116 is different from the right side. Also, the nasal shield aperture 108 is not in the center of the convex curved surface 116.

FIG. 1B is an exploded three-quarter view line drawing of the cannula embodiment 100 depicted in FIG. 1A. As shown, the cannula embodiment 100 generally comprises a cannula 114 that has a first cannula post 124A and a second cannula post 124B, both extending from the center cylinder 115, wherein each of the cannula posts 124A/124B define an outlet port 110 at the post terminating ends 125A and 125B, respectively. An intake tube sleeve 118 extends from the first center cylinder end 120A and another intake tube sleeve 118 extends from a second center cylinder end 120B. The first nasal shield 106A is configured to matingly engage with the first cannula post 124A at the first post terminating end 125A and the second nasal shield 106B is configured to matingly engage with the second cannula post 124B of the second post terminating end 125B, as shown in FIG. 1A. The first and second nasal shields 106A/106B, each have a nasal shield aperture 108A/108B that aligns with the respective outlet ports 110A/110B. The intake tubes 102 engage the receiving port 122 in the intake tube sleeve 118.

FIG. 2A is a line drawing illustratively depicting a front view of the cannula embodiment 100 connected to an oxygen source consistent with embodiments of the present invention. As shown, oxygen 112 from the oxygen source 130 is directed through the intake tubes 102, through the intake tube sleeves 118 and into the center cylinder 115 where the oxygen 112 flows through the cannula posts 124 and out from the cannula outlet ports 110. As discussed earlier, the nasal shields 106, which resemble mushroom caps, press against a person's nostrils 604 to block the oxygen 112 from flowing out of the person's nose 610. In this way, oxygen 112 is more consistently provided to the patient using the cannula 100.

Figure 2B:
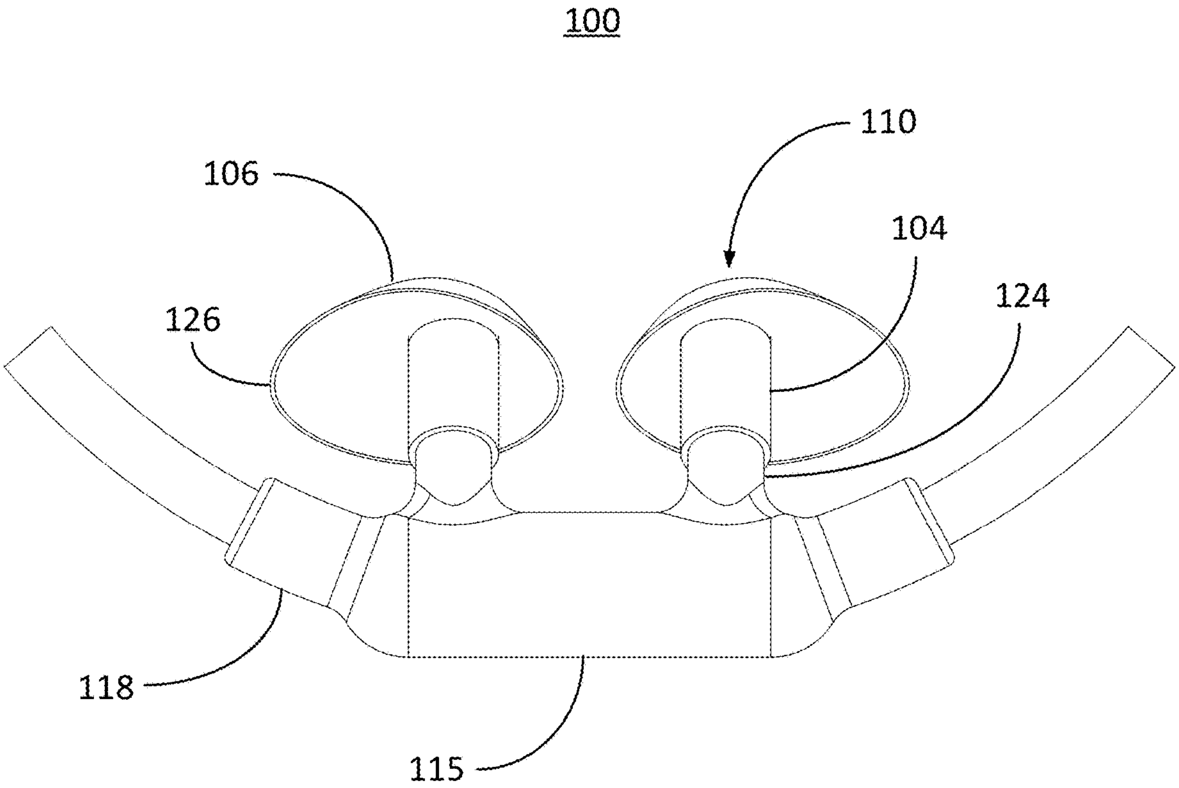
FIG. 2B is a line drawing illustratively depicting a back view of the cannula embodiment.

FIG. 2B is a line drawing back view of the cannula embodiment 100. As shown here, each of the nasal shields 106 comprise a cannula post sleeve 104 that slides over at least a portion of the cannula post 124. The cannula sleeves 104 retain the nasal shields 106 on the cannula posts 124. Certain embodiments envision the intake tube sleeves 118, the center cylinder 115, and the cannula posts 124 being molded from a single piece of polymer. In other words, the elements 118, 115 and 124 are of unitary construction as opposed to different pieces connected and/or adhered to one another.

Figure 3:
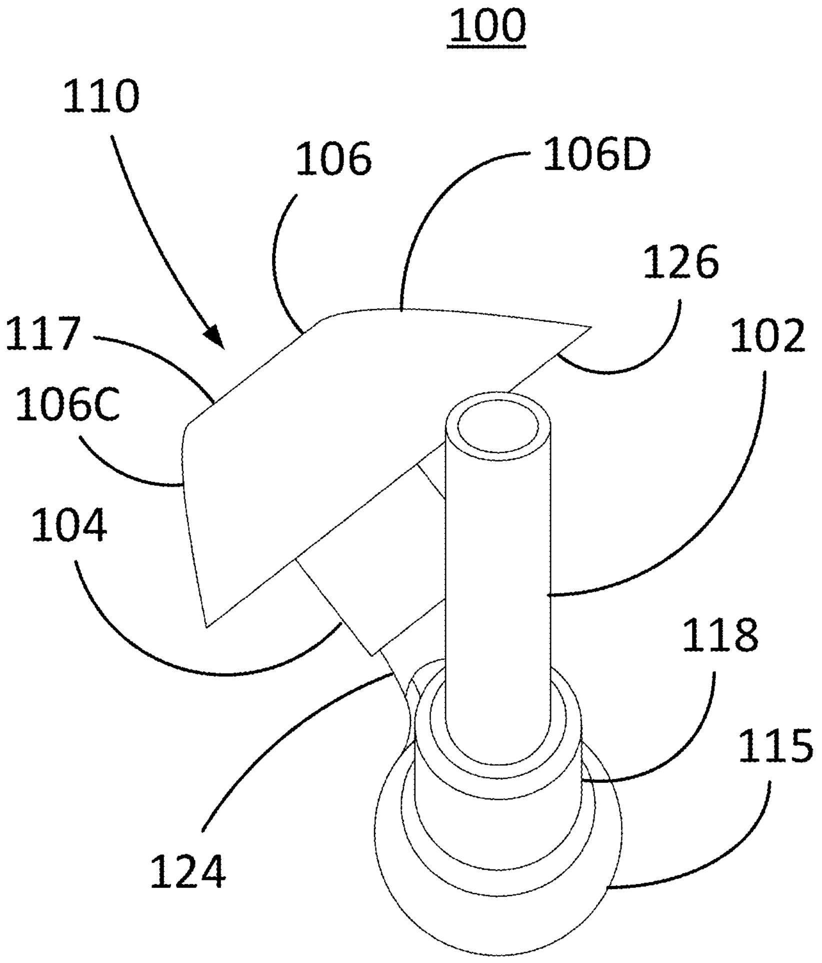
FIG. 3 is a side view line drawing of the cannula embodiment of FIGS. 1A and 1B.

FIG. 3 is a side view line drawing of the cannula embodiment 100. As shown here, the cannula post sleeve 104 is covering/overlapping a portion of the cannula post 124. Also, in this embodiment the nasal shield 106 is not symmetric about the cannula post 124. That is, the nasal shield 106 is longer from the convex curved surface apex 117 to the shield periphery 126 on the nasal shield portion to the right 106D as compared to the nasal shield portion to the left 106C. For reference, the cannula outlet port 110 location is shown along with the center cylinder 115, the intake tube sleeve 118 and intake tube 102.

Figure 4A:
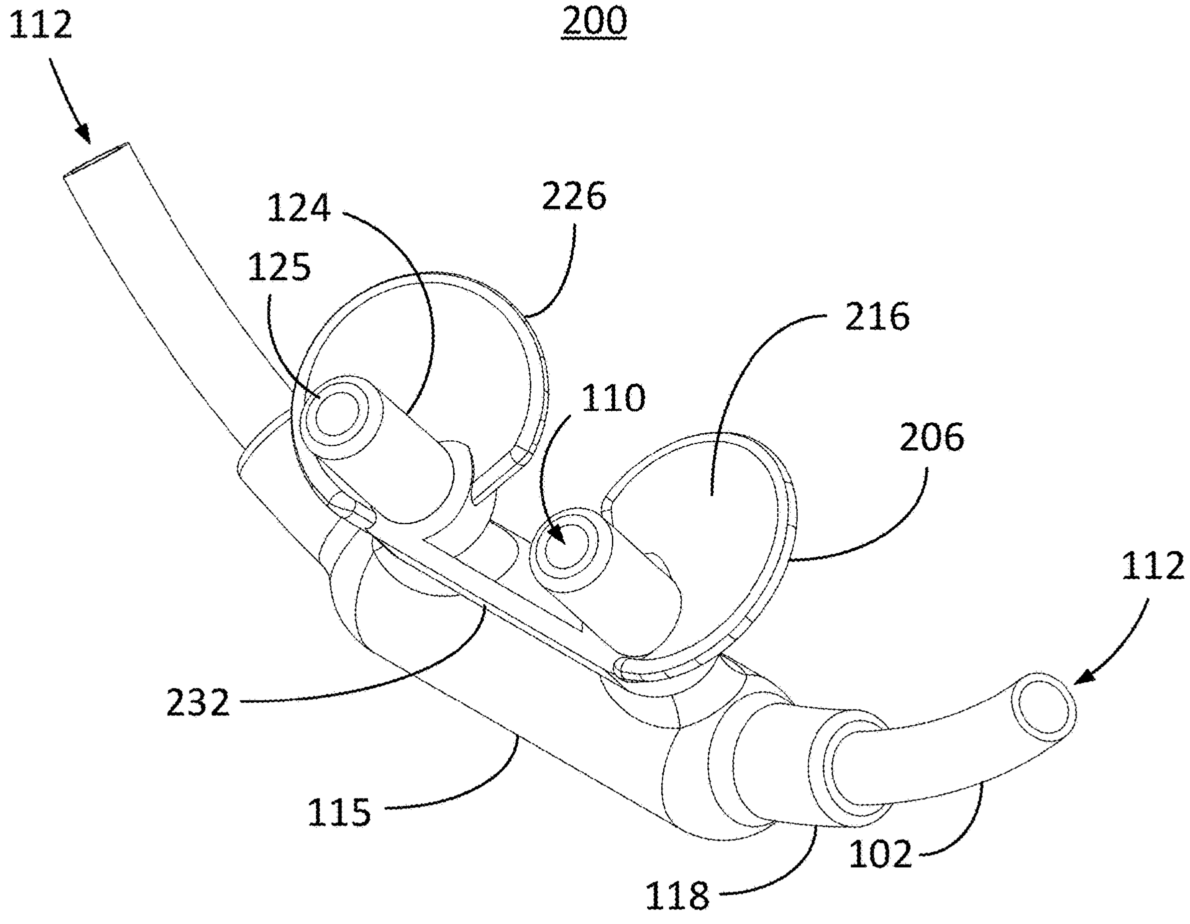
FIGS. 4A and 4B are line drawings of another low leakage nasal cannula embodiment consistent with embodiments of the present invention.
Figure 4B:
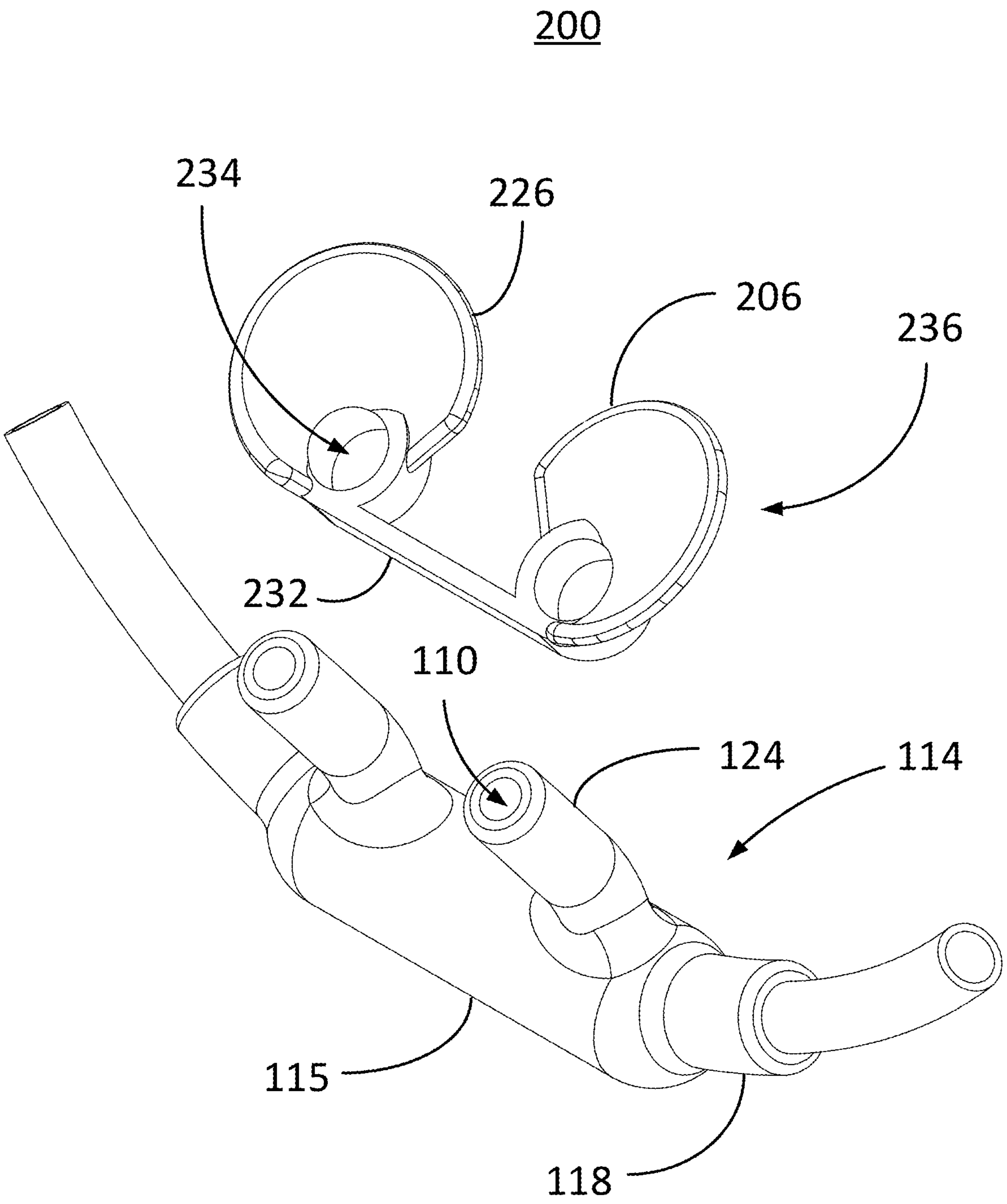

FIGS. 4A and 4B are line drawings of another low leakage nasal cannula embodiment consistent with embodiments of the present invention. FIG. 4A is a three-quarter view line drawing of the low leakage nasal cannula embodiment 200, which is a concave shielded nasal cannula embodiment 200, or simply "cannula 200" with the cannula posts 124 extending out from the nasal shields 206. The cannula 200 generally comprises two nasal cannula shields 206 that are each attached to a corresponding cannula post 124. The two nasal cannula shields 206 are configured to help prevent oxygen leakage from the wearer's nostrils 604. As shown in FIGS. 4A and 4B, the cannula 200 generally comprises a pair of cannula posts 124 extending orthogonally from a center cylinder 115. Each cannula post 124 defines an outlet port 110 at a post terminating end 125. Oxygen 112, from an oxygen source 130 shown in FIG. 5A, flows through the oxygen tubes 102, into the cannula 200 and out/exits through the outlet ports 110. The oxygen tubes 102 connect to intake tube sleeves 118 on either end 120 of the center cylinder 115.

The pair of nasal shields 206 are generally defined by outward facing concave/cupped surfaces 216 that interface nostrils 604. Each of the nasal shields 206 when attached to the corresponding cannula posts 124 resemble the shape of a radar dish. In certain embodiments, the nasal shields 206 are a soft pliable polymer, such as rubber or latex, for example, while in other embodiments the nasal shields 206 are stiff. The cannula posts 124 can be a relatively stiff polymer that essentially retain their shape when in use, such as PVC or some other suitable material. Each cupped surface 216 comprises a shield periphery 226 that extends beyond the opening of a nostril 604 thereby blocking the nostril 604. In this arrangement, no portion of the cupped surface 216 penetrates the distal portion of the nostril 604. Oxygen 112 enters the nasal cavity via the cannula outlet ports 110 that penetrate into the nasal cavity. In this embodiment, the two nasal shields 20 are connected by way of a joining bar 232. In the present embodiment, at least 20% of the cannula posts 124 extend from the concave surface 216. Optionally, at least 50% of the cannula posts 124 extend from the concave surface 216.

FIG. 4B is a line drawing of an exploded three-quarter view of the cannula embodiment 200 depicted in FIG. 4A. As shown, the cannula embodiment 200 generally comprises the cannula 114 of FIGS. 1A-3. Two cannula posts 124 extend from the center cylinder 115, each defining the outlet port 110 at the respective post terminating ends 125. As previously discussed, the intake tube sleeves 118 extends from the center cylinder ends 120. Each of the nasal shields 206 comprise a receiving aperture 234 that receive a corresponding cannula post 124. As shown the two nasal shields 206 are connected via the nasal shield joining bar 234, which collectively form a nasal shield module 236. Nasal shield module 236 is already pre-spaced apart and will that over the cannula posts 124 the appropriate position. Other embodiments envision no nasal shield joining bar 232, rather individual nasal shields 206 that fit into place over the nasal cannula posts 124 and the appropriate position.

Figure 5A:
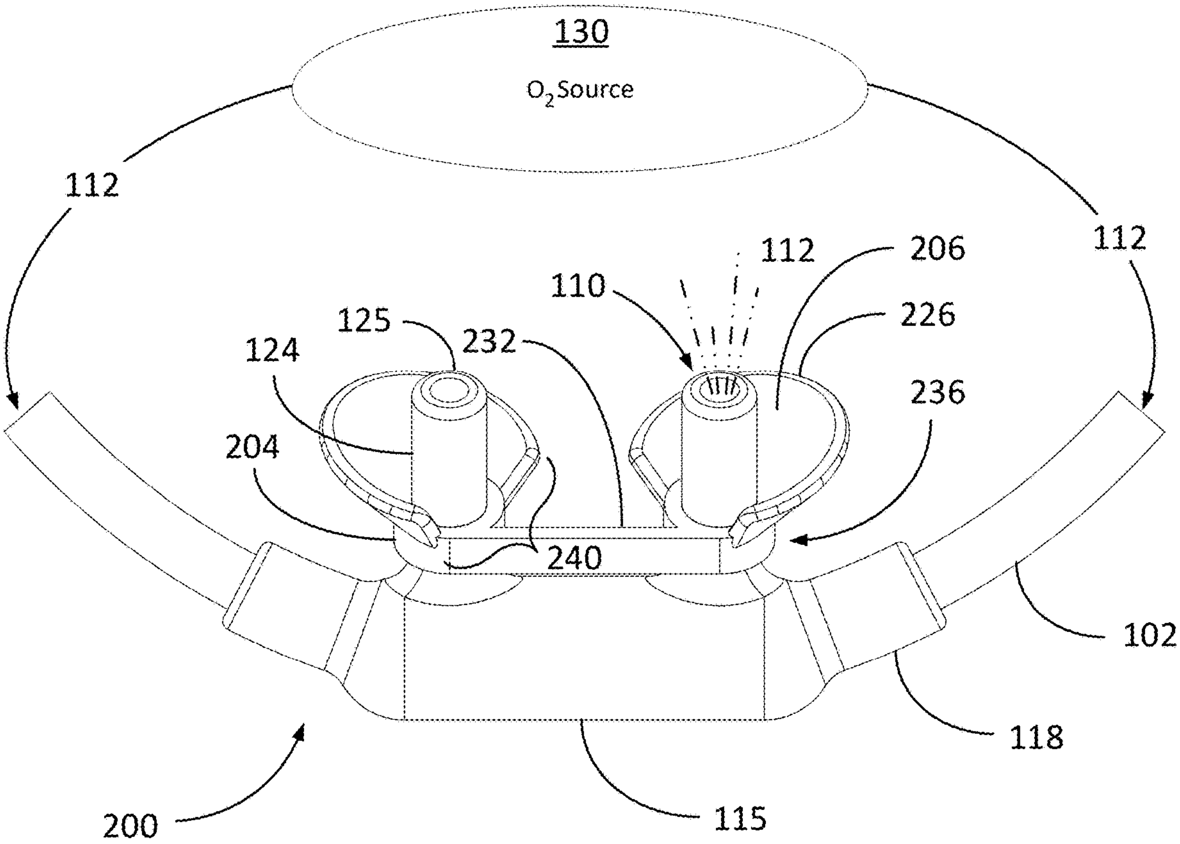
FIG. 5A is a line drawing illustratively depicting a front view of the cannula embodiment of FIGS. 4A and 4B connected to an oxygen source consistent with embodiments of the present invention.

FIG. 5A is a line drawing illustratively depicting a front view of the cannula embodiment 200 connected to an oxygen source consistent with embodiments of the present invention. As shown, oxygen 112 from the oxygen source 130 is directed through the intake tubes 102, through the intake tube sleeves 118 and into the center cylinder 115. Oxygen 112 flows from the center cylinder 115 through the cannula posts 124 and out from the cannula outlet ports 110. As discussed earlier, the nasal shields 206 press against a person's nostrils 604 to block the oxygen 112 from flowing out of the person's nose 610. In this way, oxygen 112 is more consistently provided to the patient using the cannula 200. The nasal shield module 236 and the shape of the cupped nasal shields 206 are shown. In this embodiment, the cupped nasal shields 206 are not full cups but rather partially cupped with a wedge gap 240 that includes where the nasal shield joining bar 232 connects to the cannula posts sleeves 204. In other words, the shield periphery 226 extends from the nasal shield joining bar 232 and then forms a curved periphery as shown. The shield periphery 226 is not a closed loop.

Figure 5B:
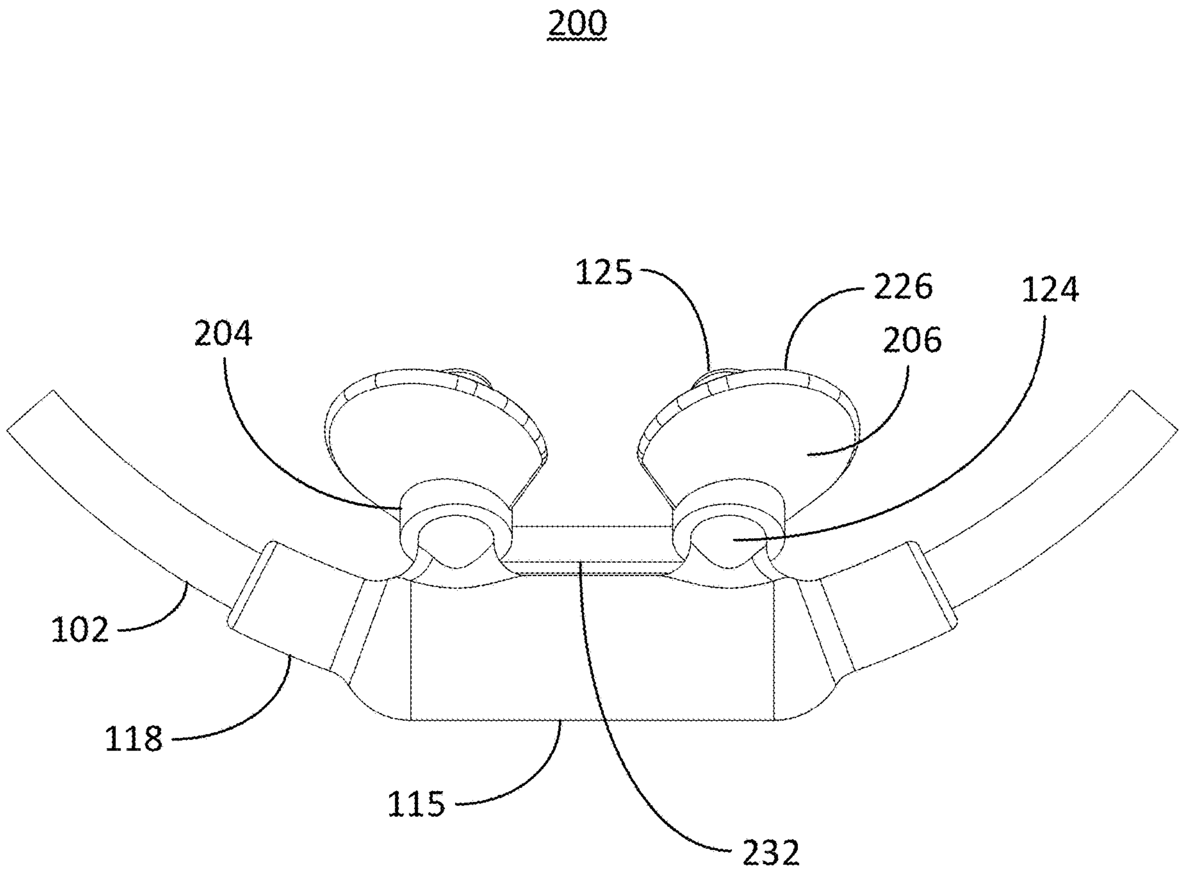
FIG. 5B is a line drawing illustratively depicting a back view of the cannula embodiment of FIGS. 4A and 4B.

FIG. 5B is a back view a line drawing of the cannula embodiment 200. In this embodiment, the nasal shield module 236 is disposed within the bottom 20% of the cannula posts 124. As shown from this angle, a pair of cannula post sleeves 204 extend from the nasal shields 206 and slidingly engage the cannula posts 124. Also in this embodiment, the nasal shield joining bar 232 connects the two cannula post sleeves 204. For reference, the post terminating end 125 is depicted along the edge of the shield periphery 226. Also shown for reference are the intake tubes 102, a tube sleeves 118, and the center cylinder 115.

Figure 6:
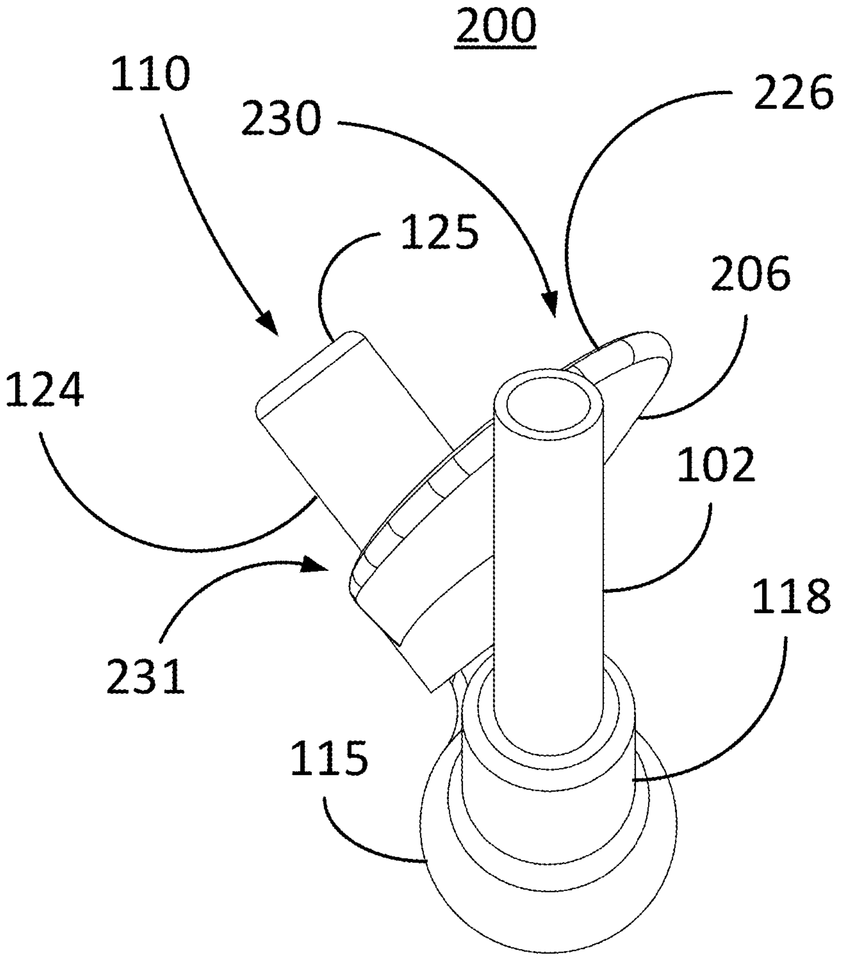
FIG. 6 is a side view line drawing of the cannula embodiment of FIGS. 4A and 4B.

FIG. 6 is a side view line drawing of the cannula embodiment 200. As shown here, the cannula post 124 extends from the cannula shield 206, which is partially obscured by the intake tube 102. Also, in this embodiment the nasal shield 206 is not symmetric about the cannula post 124. That is, the nasal shield 206 is longer from the cannula post 124 to the shield periphery 226 on the right-hand side 230 of the from the nasal shield 206. The nasal shield 206 is shorter and partly devoid where the shield wedge gap 240, of FIG. 5A, is on the left-hand side 231 compared to the right-hand side 230. For reference, the cannula outlet port 110 location is shown along with the center cylinder 115, the intake tube sleeve 118 and intake tube 102.

Figure 7A:
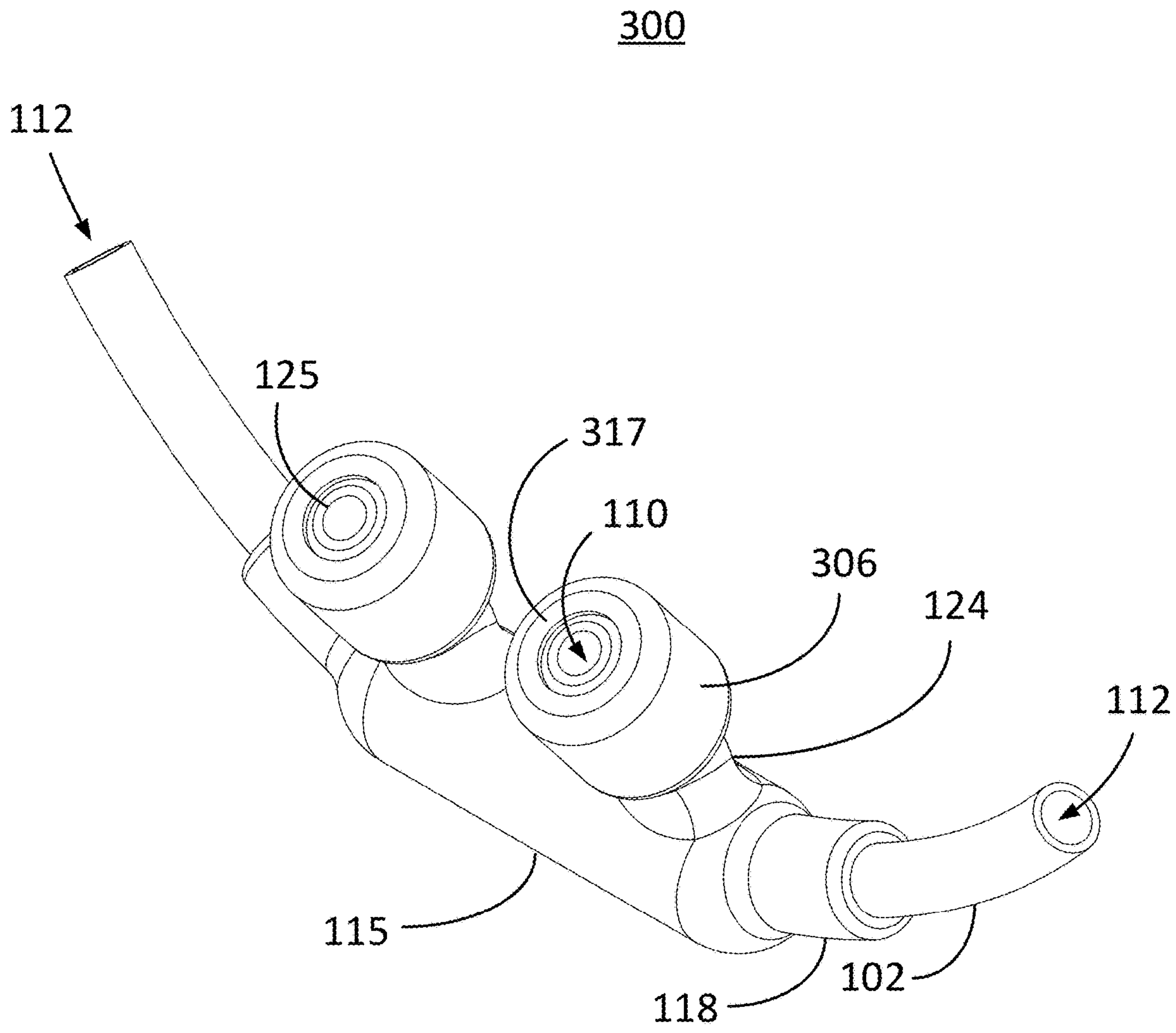
FIGS. 7A and 7B are line drawings of yet another low leakage nasal cannula embodiment consistent with embodiments of the present invention.
Figure 7B:
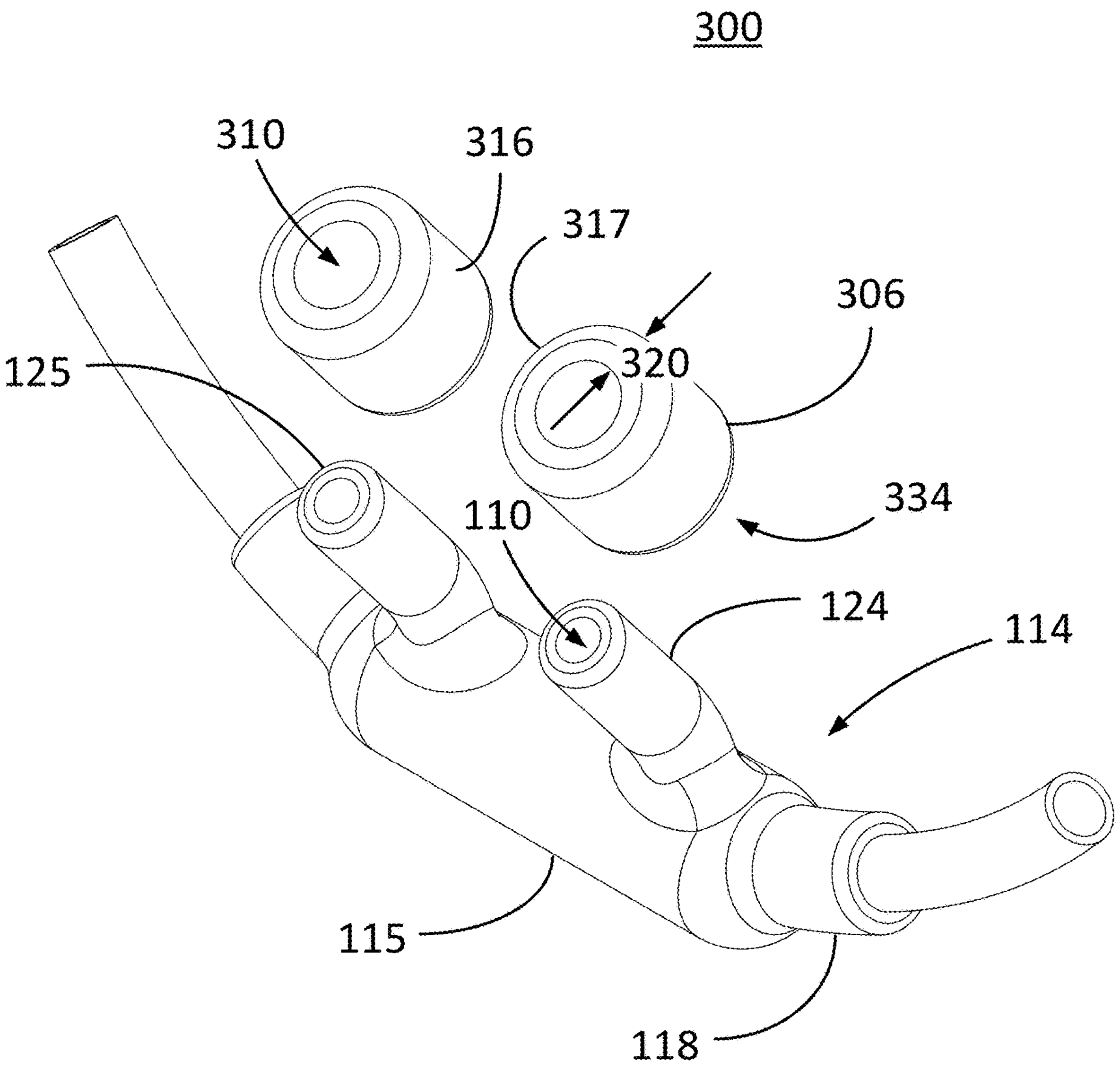
Figure 8A:
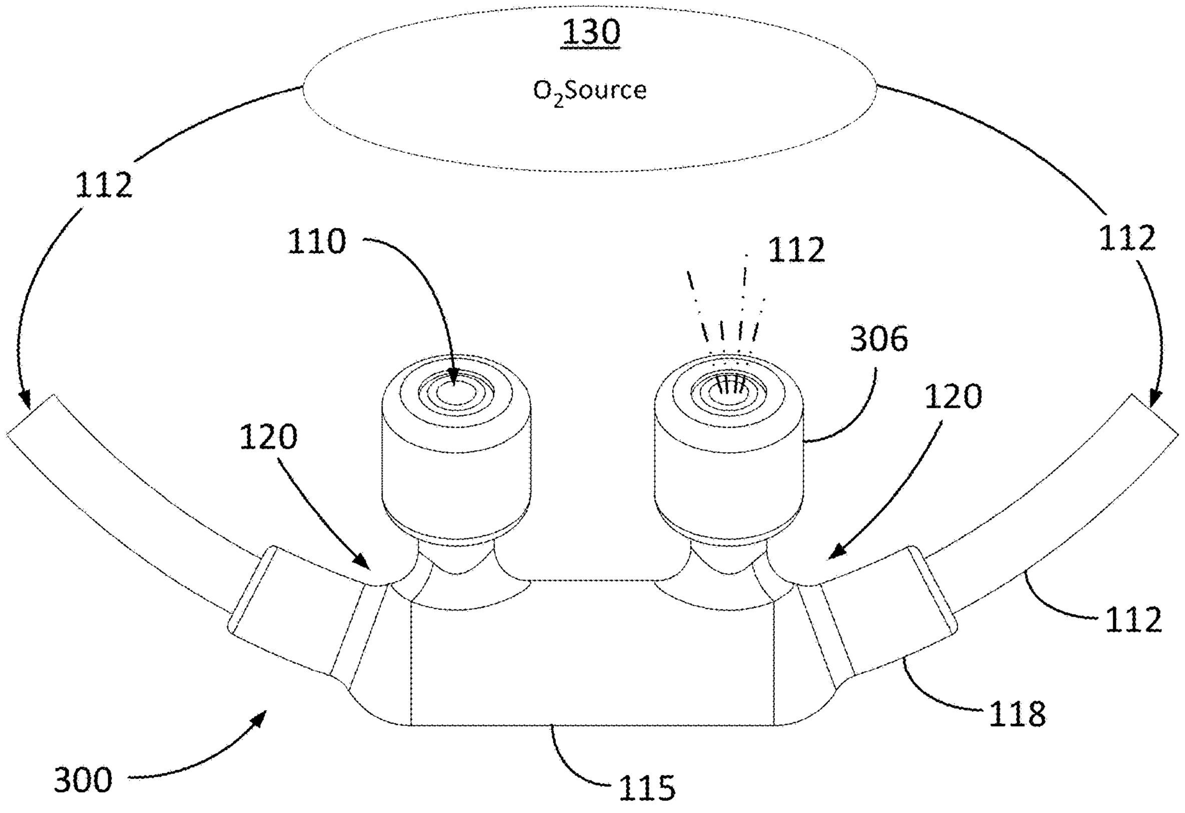
FIG. 8A is a line drawing illustratively depicting a front view of the cannula embodiment of FIGS. 7A and 7B connected to an oxygen source consistent with embodiments of the present invention.

FIGS. 7A and 7B are line drawings of yet another low leakage nasal cannula embodiment consistent with embodiments of the present invention. FIG. 7A is a three-quarter view line drawing of the low leakage nasal plug nasal cannula embodiment 300, or simply "cannula 300". The cannula 300 generally comprises two nasal cannula plugs 306 that are each attached to a corresponding cannula post 124. The two nasal cannula plugs 306 are configured to help prevent oxygen leakage from the wearer's nostrils 604. As shown in FIGS. 7A and 7B, the cannula 300 generally comprises a pair of cannula posts 124 extending orthogonally from a center cylinder 115. Each cannula post 124 defines an outlet port 110 at a post terminating end 125. Oxygen 112, from an oxygen source 130 as shown in FIG. 8A, flows through the oxygen tubes 102, into the cannula 300 and out through the outlet ports 110. The oxygen tubes 102 connect to intake tube sleeves 118 on either end 120 of the center cylinder 115.

The pair of nasal cannula plugs 306 can be pliable cylinders 316 that interface and plug a wearer's nostrils 604. Each of the nasal cannula plugs 306 tightly conform to a corresponding on of the cannula posts 124 when attached. In certain embodiments, the nasal cannula plugs 306 are a soft pliable polymer, such as rubber or latex, for example, while in other embodiments the nasal cannula plugs 306 are foam, like ear plugs. The cannula posts 124 can be a relatively stiff polymer, made from PVC or some other suitable material. Each nasal cannula plug 306 is defined by a cylinder 316 that has a cylinder thickness 320 sized to plug a nostril thereby blocking the nostril to prevent oxygen 112 from escaping out from the wearer's nose 610. Though these plugs are cylindrical shaped, other nasal cannula plugs 306 are envisioned to be tapered, rounded on the ends and wider close to the center cylinder 115, or some other shape that can accomplish plugging the nostril 604. In a preferred embodiment, wherein the nasal cannula plug 306 is foam, the nasal cannula plug 306 is compressed to slide into the nostril where it expands to fill the nostril diameter much like an earplug expands to fill the diameter of the ear canal. In this way, over the course of several seconds, each nostril plug 306 closes off the nostril 604. In the present embodiment, the majority (at least 80%) of the cannula post 124 is surrounded by the nasal cannula plug 306. Optionally, at least 50% of the cannula posts 124 is surrounded by the nasal cannula plug 306. In the present embodiment, the nasal plug distal surface 317 extends slightly beyond the cannula post terminating end 125, within 10% of the length of the cannula post 124. Other embodiments contemplate the nasal plug distal surface 317 being slightly shy (or short) of the cannula post terminating end 125, within 10% of the length of the cannula post 124.

FIG. 7B is an exploded three-quarter view line drawing of the cannula embodiment 300 depicted in FIG. 7A. As shown, the cannula embodiment 300 generally comprises the cannula 114 of FIGS. 1A-3. Two cannula posts 124 extend from the center cylinder 115 to the outlet port 110 at the respective post terminating ends 125. As previously discussed, the intake tube sleeves 118 extends from the center cylinder ends 120. Each of the nasal cannula plugs 306 comprise a receiving aperture 334 that receive a corresponding cannula post 124, wherein the nasal cannula plugs 306 slide over and conform to the cannula posts 124 like a sleeve.

FIG. 8A is a line drawing illustratively depicting a front view of the cannula embodiment 300 connected to an oxygen source consistent with embodiments of the present invention. As shown, oxygen 112 from the oxygen source 130 is directed through the intake tubes 102, through the intake tube sleeves 118 and into the center cylinder 115. From the center cylinder 115, oxygen 112 flows through the cannula posts 124 and out from the cannula outlet ports 110. As discussed earlier, the nasal cannula plugs 306 can be made to expand inside of a person's nostrils 604 to block the oxygen 112 from flowing out of the person's nose 610. In this way, oxygen 112 is more consistently and evenly provided to the patient using the cannula 300.

Figure 8B:
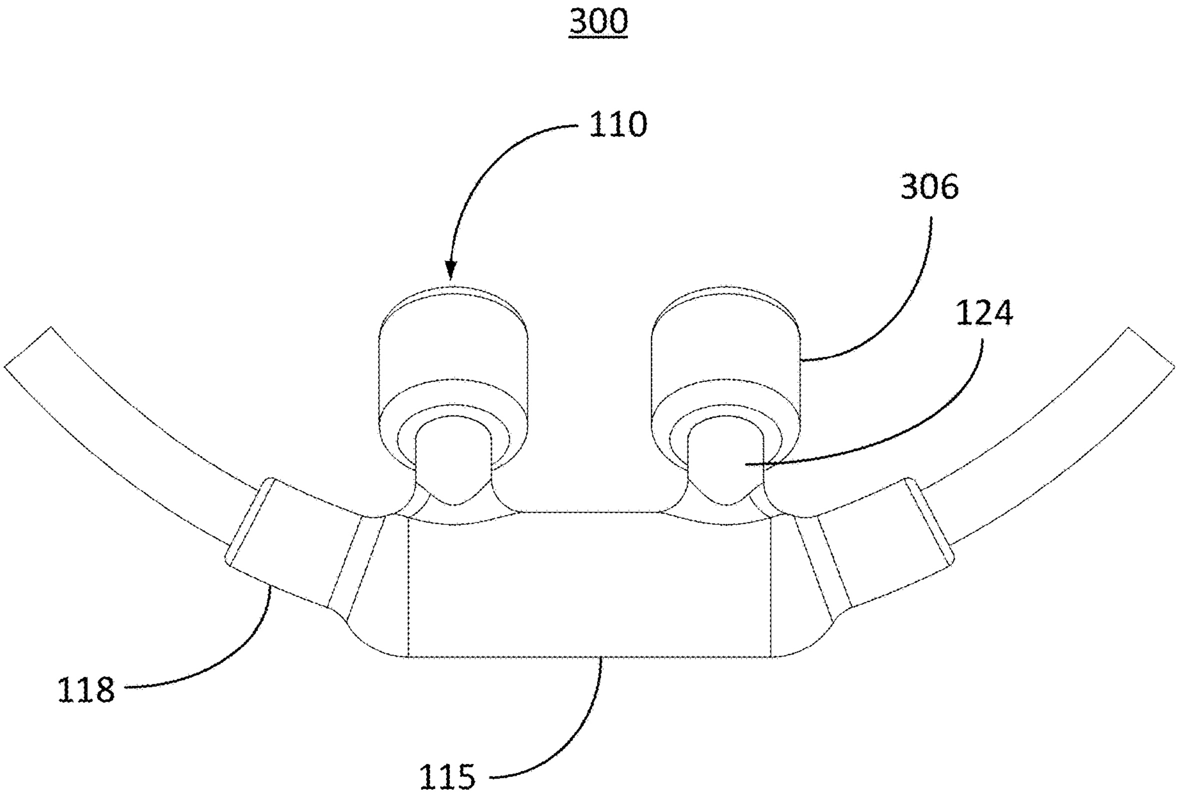
FIG. 8B is a line drawing illustratively depicting a back view of the cannula embodiment of FIGS. 7A and 7B.

FIG. 8B is a line drawing illustratively depicting a back view of the cannula embodiment 300. In this embodiment, the nasal cannula plugs 306 are disposed along the cannula post 124 up to about the bottom 20% of the cannula posts 124. Other embodiments envision that the nasal cannula plugs 306 mostly reside along the top of the cannula posts 124 but are within 50% of where the cannula posts 124 meet the center cylinder 115. For reference, the intake tubes 102, a tube sleeves 118, and the center cylinder 115 are shown.

Figure 9:
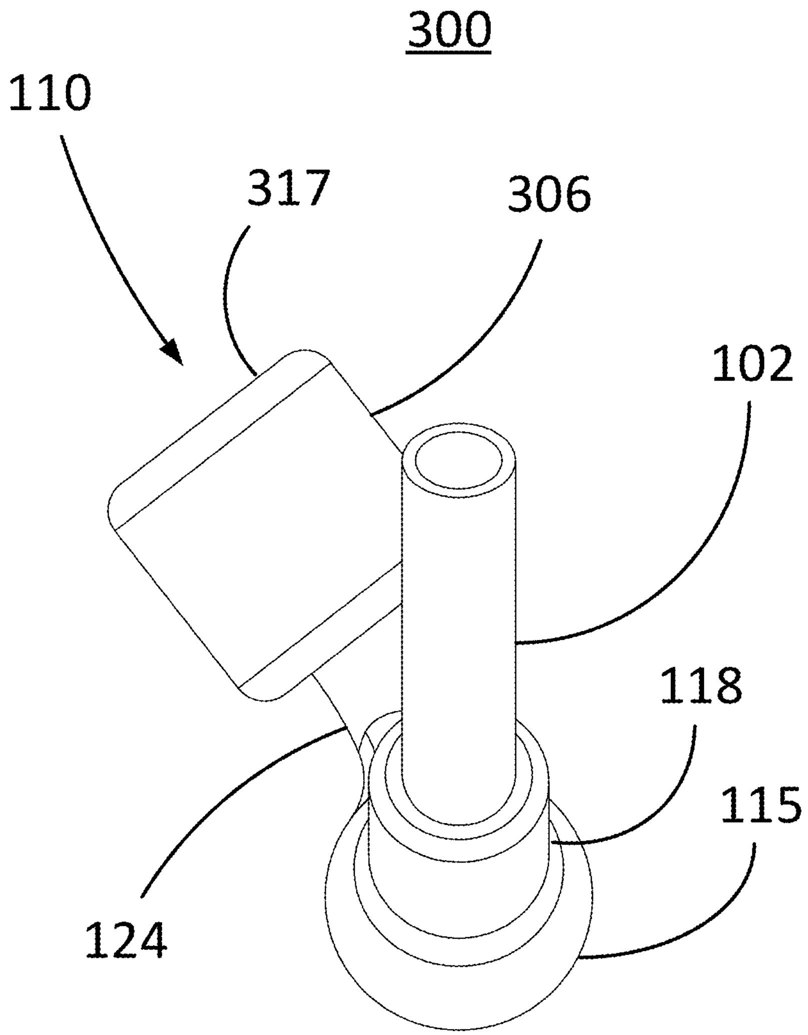
FIG. 9 is a side view line drawing of the cannula embodiment of FIGS. 7A and 7B consistent with embodiments of the present invention.

FIG. 9 is a side view line drawing of the cannula embodiment 300. As shown here, the nasal cannula plugs 306 extend along at least 50% of the cannula post 124 from the center cylinder 115, which is partially obscured by the intake tube 102. Also, in this embodiment, the nasal plug distal surface 317 is at or beyond the most distal portion of the cannula post 124. For reference, the cannula outlet port 110 location is shown along with the center cylinder 115, the intake tube sleeve 118 and intake tube 102.

Figure 10A:
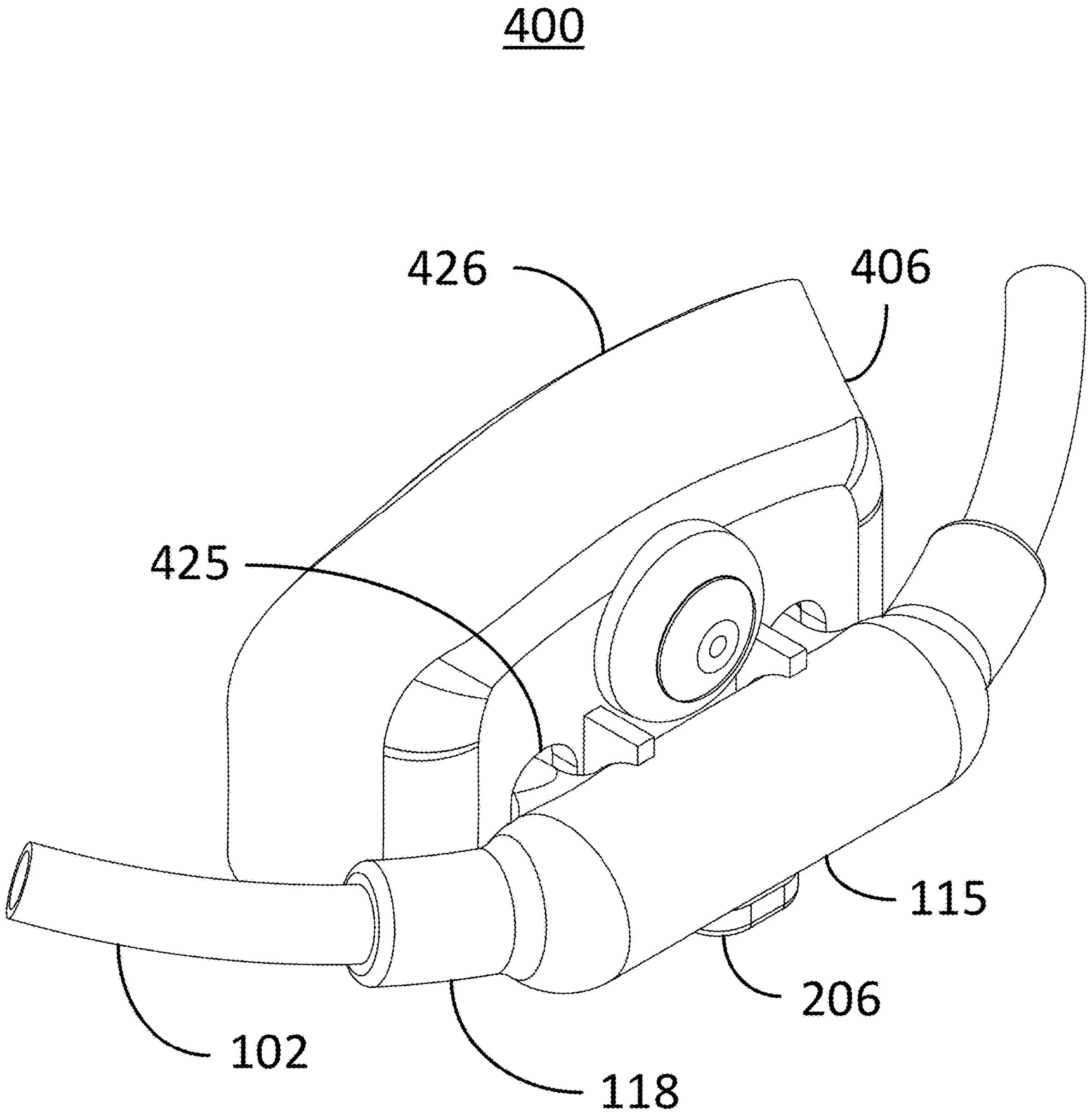
FIGS. 10A and 10B are line drawings of another low leakage nasal cannula embodiment consistent with embodiments of the present invention.
Figure 10B:
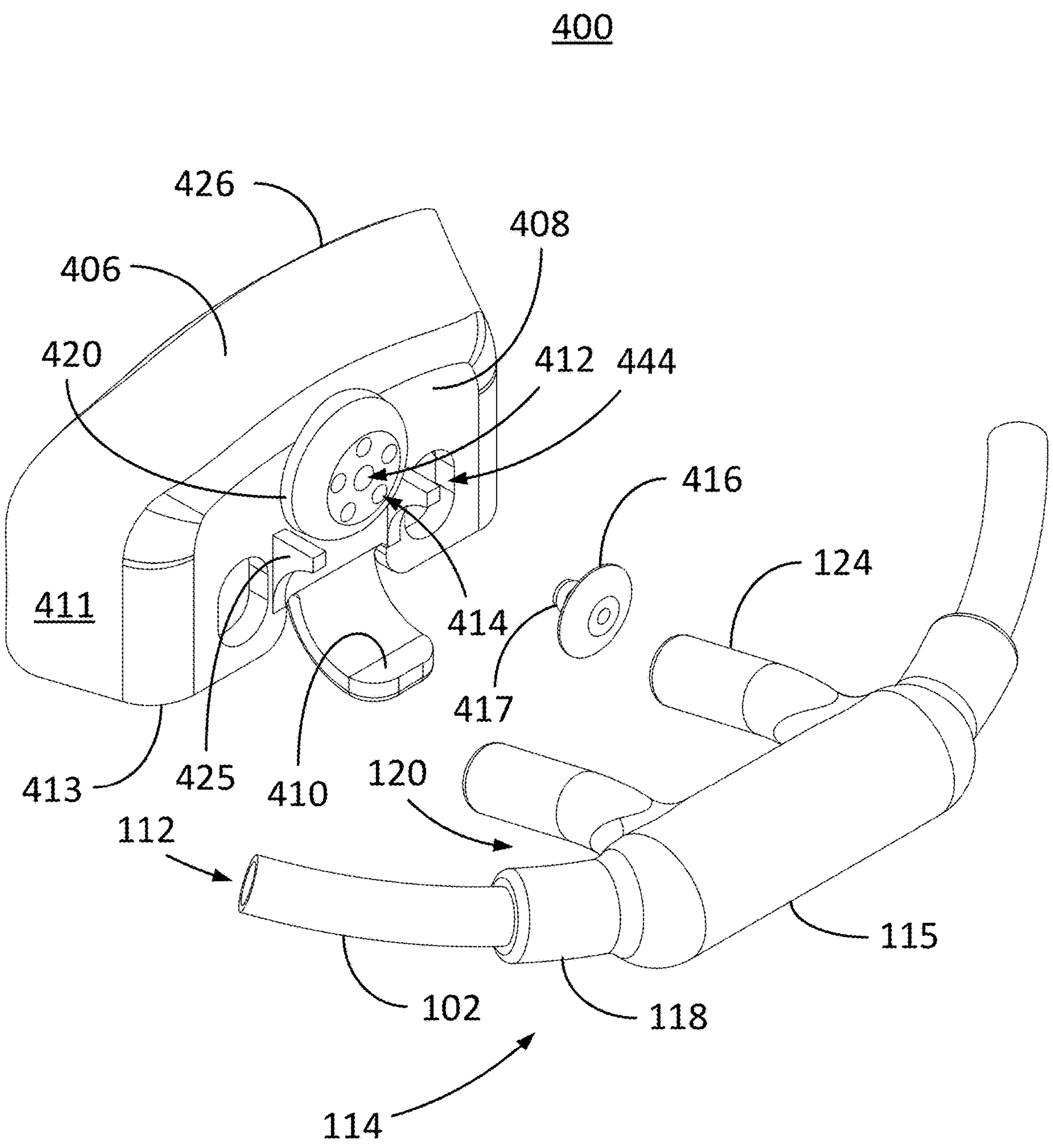

FIGS. 10A and 10B are line drawings of another low leakage nasal cannula embodiment consistent with embodiments of the present invention. FIG. 10A is an offset angle view line drawing of the low leakage nasal cup/shielded cannula embodiment 400 or simply "nasal cup cannula 400". As shown in FIG. 10B, cannula posts 124 extend orthogonally from a center cylinder 115 into a cup 406 that covers a person's nostrils 604 and surrounding area of their nose tip 618 (underneath part of a person's nose 612 where their nostrils 604 are located just above the philtrum 615). The nasal cup 406 is defined by a perimeter 426 that covers between 50% and 100% of the bottom of a person's nose 612 to help shield oxygen flowing from the cannula 114, which reduces oxygen leakage from the wearer's nostrils 604. Each cannula post 124 defines an outlet port 110 at a post terminating end 125. Oxygen 112, from an oxygen source 130, as shown in FIG. 5A, flows through the oxygen tubes 102, into the nasal cup cannula 400 through the outlet ports 110. The oxygen tubes 102 connect to the intake tube sleeves 118 on either end 120 of the center cylinder 115.

The nasal cup 406 "cups" over at least a portion of the bottom of a wearer's nose 612 and nostrils 604 with the cannula posts 124 penetrating the nostrils 604. Though in some circumstances, oxygen 112 may leak from the nasal cup 406, a large portion of the oxygen 112 is channeled into the wearer's nostrils 604. More specifically, oxygen 112 enters the nasal cavity via the cannula outlet ports 110 that penetrate the nasal cavity. The nasal cup 406 can be a soft pliable polymer, such as a flexible PVC, for example, while in other embodiments the nasal cup 406 is stiff. The cannula posts 124 can be a relatively stiff polymer, from rigid to being able to bend if manipulated by the wearer. The cannula posts 124 can be made from PVC or some other suitable material. The nasal cup 406 can be opaque or clear.

FIG. 10B is an exploded offset angle view line drawing of the nasal cup cannula embodiment 400 depicted in FIG. 10A. As shown, the nasal cup cannula embodiment 400 generally comprises the cannula 114 of FIGS. 1A-3. The nasal cup cannula embodiment 400 generally comprises two cannula posts 124, each extending from the center cylinder 115. Each of the cannula posts 124 defines the outlet port 110 at the respective post terminating ends 125. As previously discussed, the intake tube sleeves 118 extends from the center cylinder ends 120. The nasal cup cannula 400 comprises a lower center cylinder support 410 and a pair of upper center cylinder supports 425 that are configured to retain the cannula 114 in place because the lower center cylinder support 410 spring loads the center cylinder 115 against the upper center cylinder supports 425. The nasal cup cannula 400 comprises a pair of post receiving apertures 444 that are sized and configured to accommodate the cannula posts 124. The post receiving apertures 444 are oblong shaped to provide some play to easily receive the cannula posts 124. In the center of the nasal cup front face 408 of the nasal cup 406 is a breathing port hub 420 to which a breathing port valve cover 416 is attached via a cover peg 417 cooperating with a cover peg hole 412. The nasal cup front face 408 meets the nasal cup sides 411 via the nasal cup side-to-front interface 413. In this embodiment, there are five exhaust ports 414 that provide a passageway for exhalent (exhaled air/breath) to exit the nasal cup 406. Hence, if a person breathes out through their nose 610, the pressure of from the person exhaling will open the breathing port valve cover 416 and the exhalent will exit the exhaust ports 414.

Figure 11A:
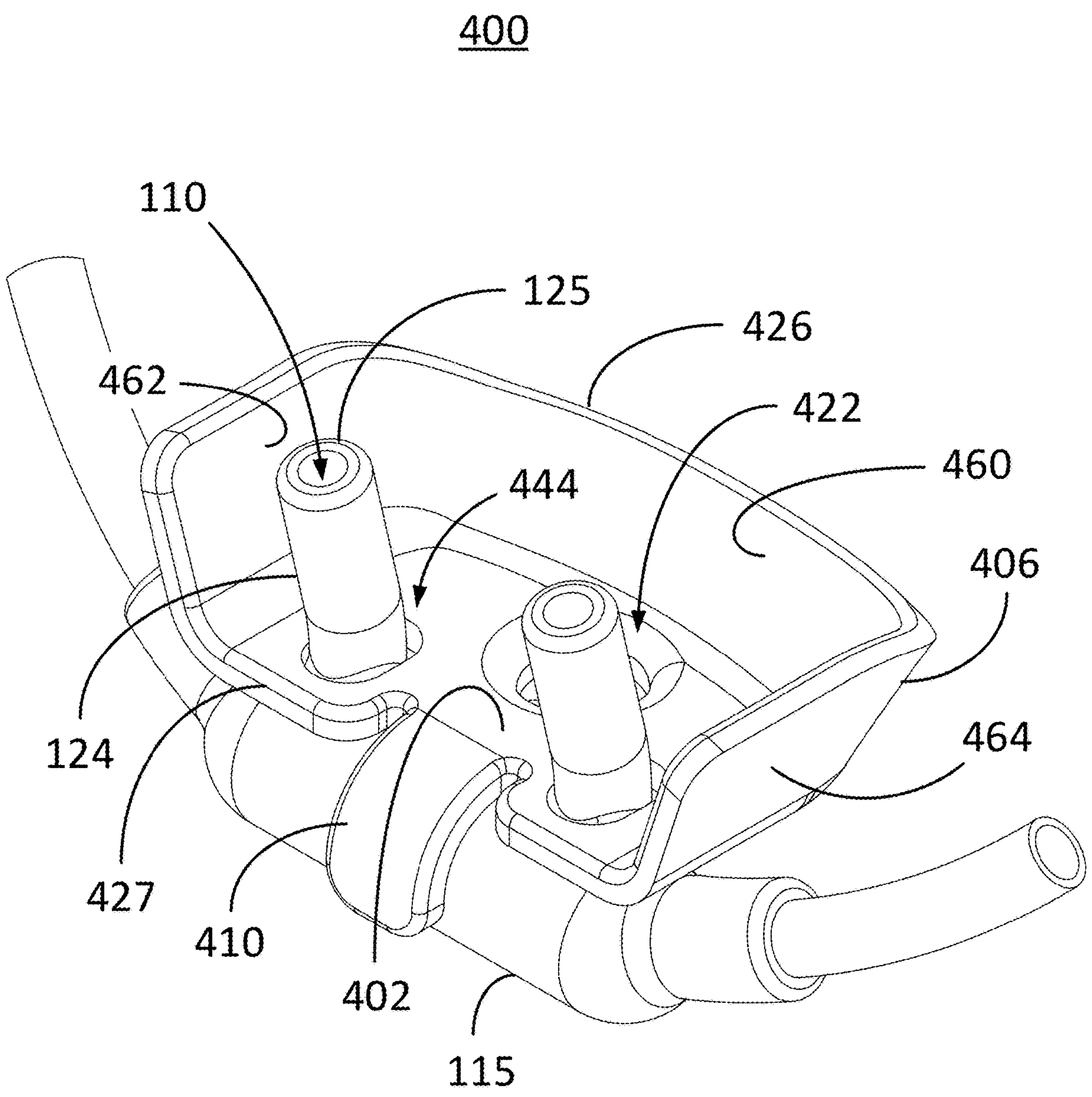
FIG. 11A is a line drawing illustratively depicting and angled inside view of the nasal cup cannula embodiment of FIGS. 10A and 10B consistent with embodiments of the present invention.

FIG. 11A is a line drawing illustratively depicting and angled inside view of the nasal cup cannula embodiment 400 consistent with embodiments of the present invention. As shown, the cannula posts 124 extend through the interior cup surface 402 of the nasal cup 406 via the post receiving apertures 444. The cannula posts 124 penetrate the wearer's nasal passage with the post terminating ends 125 inside of the nose 610 where oxygen 112 can blow into the nose 610 via the outlet port 110. The lower center cylinder support 410 is shown retaining the cannula 114 in place at the center cylinder 115. Also shown is the exhaust port region 422 that leads to the exhaust ports 414. Lastly, this figure calls out the perimeter 426, which cups around the majority of the bottom of a person's nose 610 with the philtrum perimeter 427 that interfaces a person's philtrum 615 above their upper lip 620.

Figure 11B:
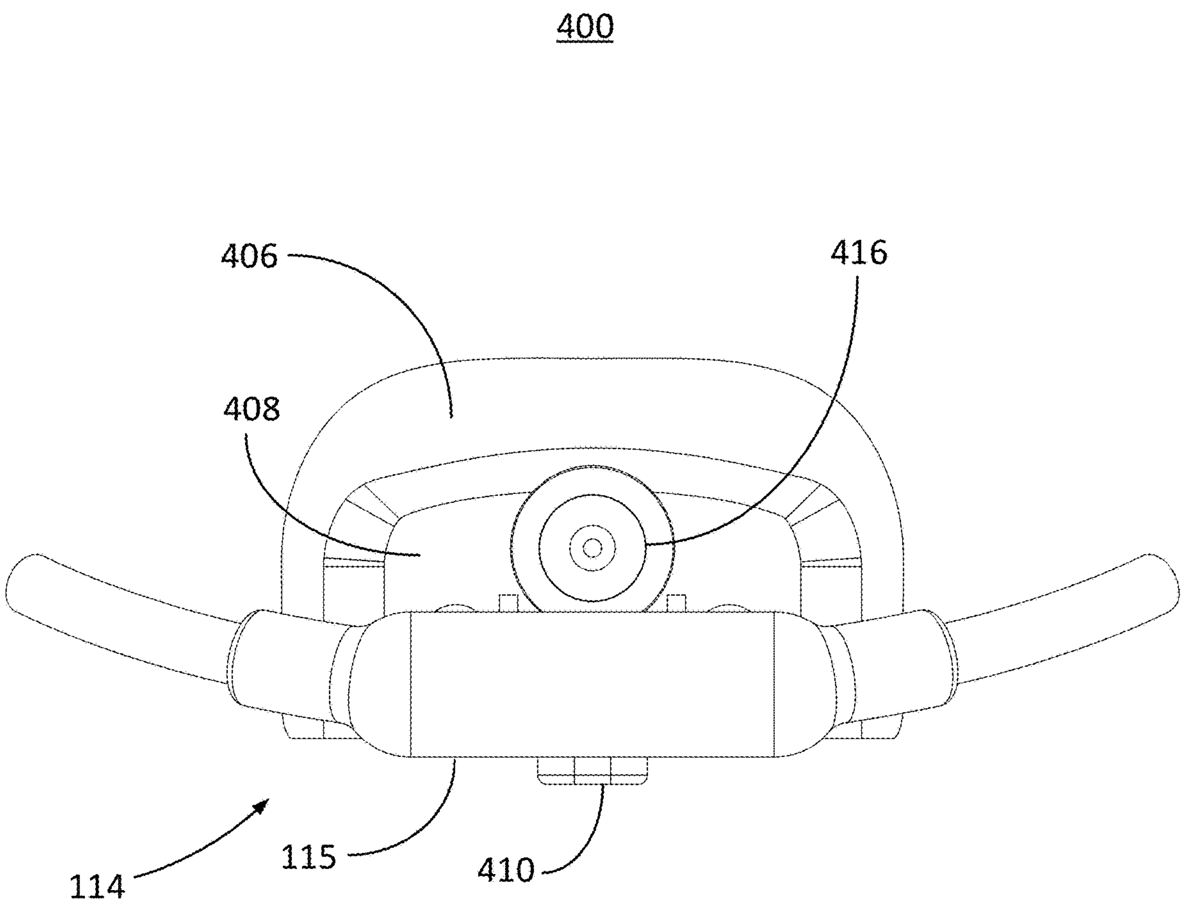
FIG. 11B is a bottom view line drawing of the nasal cup cannula embodiment of FIGS. 10A and 10B consistent with embodiments of the present invention.

FIG. 11B is a bottom view line drawing of the nasal cup cannula embodiment 400 consistent with embodiments of the present invention. This is a view as seen from looking up the wearer's nose 610 or otherwise into the wearer's nostrils

604 (or where the wearer's nose 610 would be). The nasal cup 406 is configured and adapted to cover the nose bottom 612 of the wearer's nose 610. When the wearer 600 breathes out from their nose 610, the breathing port valve cover 416 (in the nasal cup front face 408) will open allowing the exhaled breath to exit the nasal cup 406. The nasal cannula 114 is shown attached to the nasal cup 406 via the lower center cylinder support 410.

Figure 11C:
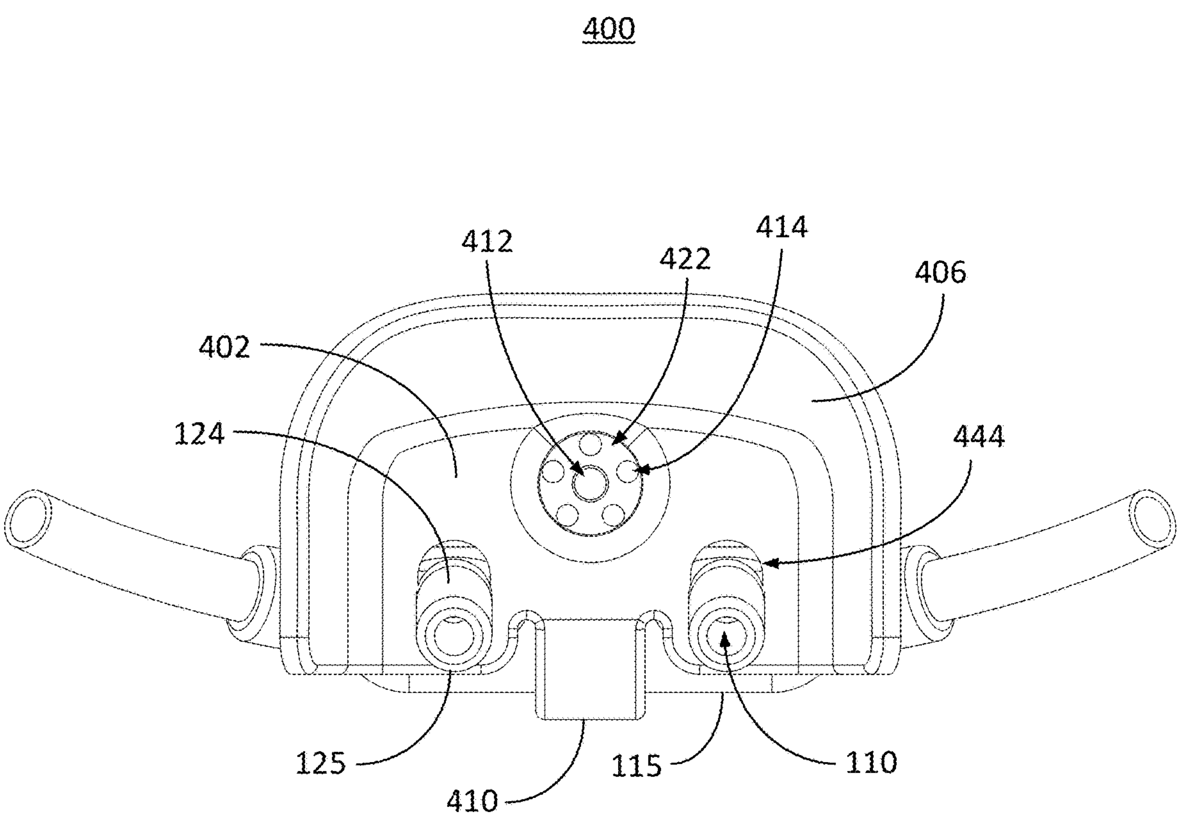
FIG. 11C is a bottom view line drawing of the nasal cup cannula embodiment from the same angle as FIG. 1B but looking out of the nasal cup interior.

FIG. 11C is a bottom view line drawing of the nasal cup cannula embodiment 400 looking out of the nasal cup interior 402 through the wearer's nostrils 604 towards the wearer's upper lip 620. The cannula posts 124 are sticking through the post receiving apertures 444 with the cannula outlet ports 110 visibly shown at the post terminating ends 125. The center cylinder 115 is retained by the lower center cylinder support 410. The exhaust port region 422 is also shown with the exhaust ports 414 and the cover peg hole 412.

Figure 11D:
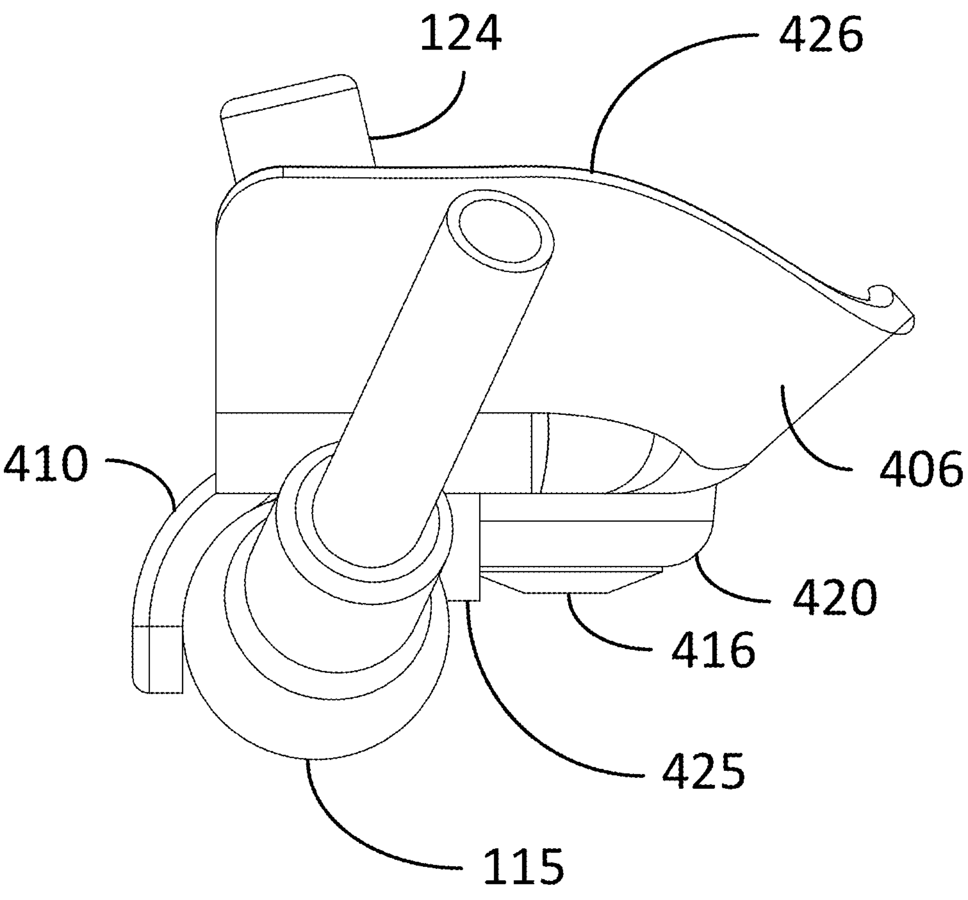
FIG. 11D is a side view line drawing of the nasal cup cannula embodiment of FIGS. 10A and 10B.

FIG. 11D is a side view line drawing of the nasal cup cannula embodiment 400. As shown the center cylinder 115 is retained by the lower center cylinder support 410 and the upper center cylinder supports 425. The cannula posts 124 are sticking through the post receiving apertures 444, wherein the cannula outlet ports 110 are visibly shown at the post terminating ends 125. The breathing port valve cover 416 is shown attached to the breathing port hub 420, both of which are attached to the nasal cup 406. Also, for reference, the cannula posts 124 are extending out from the perimeter 426.

Figure 12A:
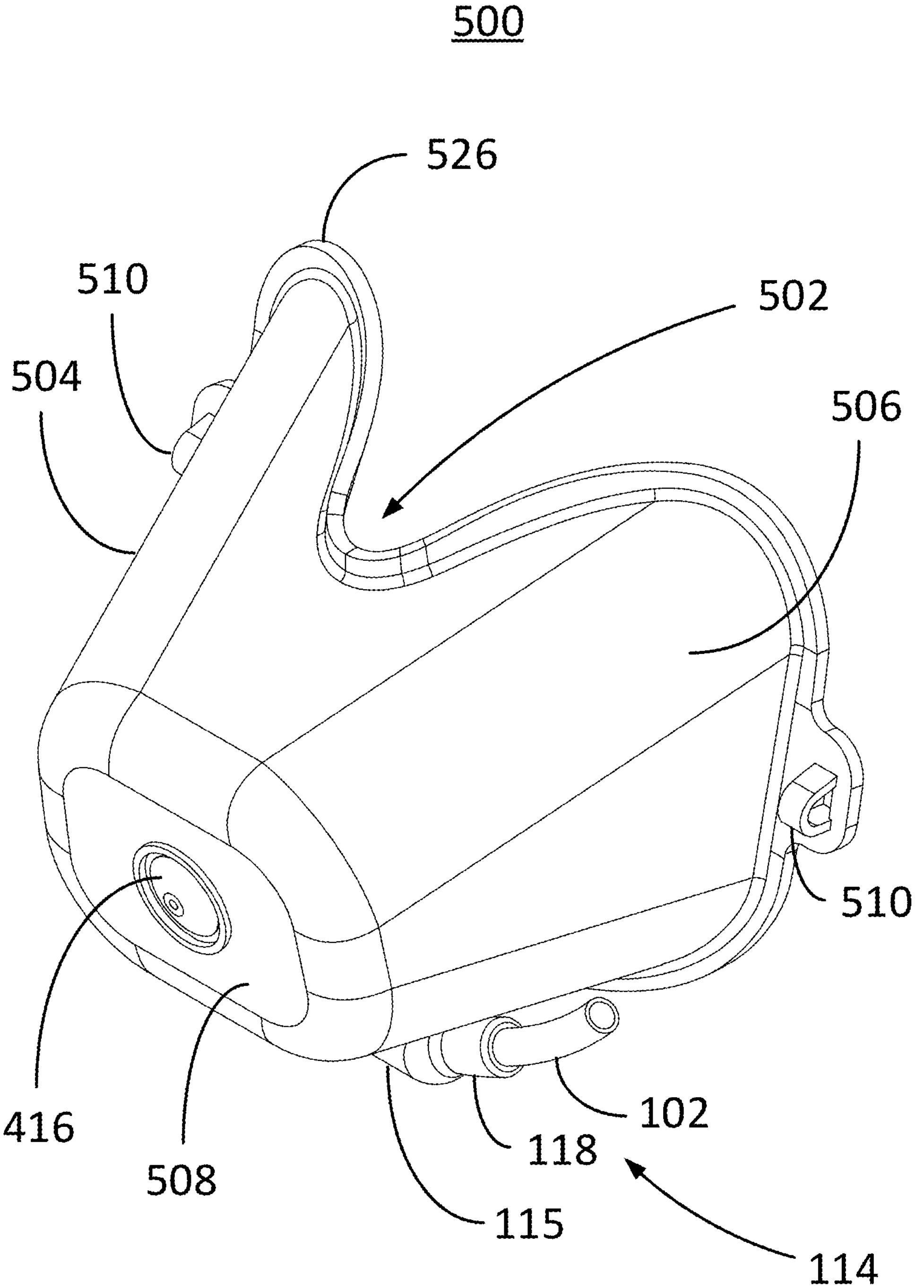
FIGS. 12A and 12B are line drawings of another low leakage nasal cannula embodiment consistent with embodiments of the present invention.
Figure 12B:
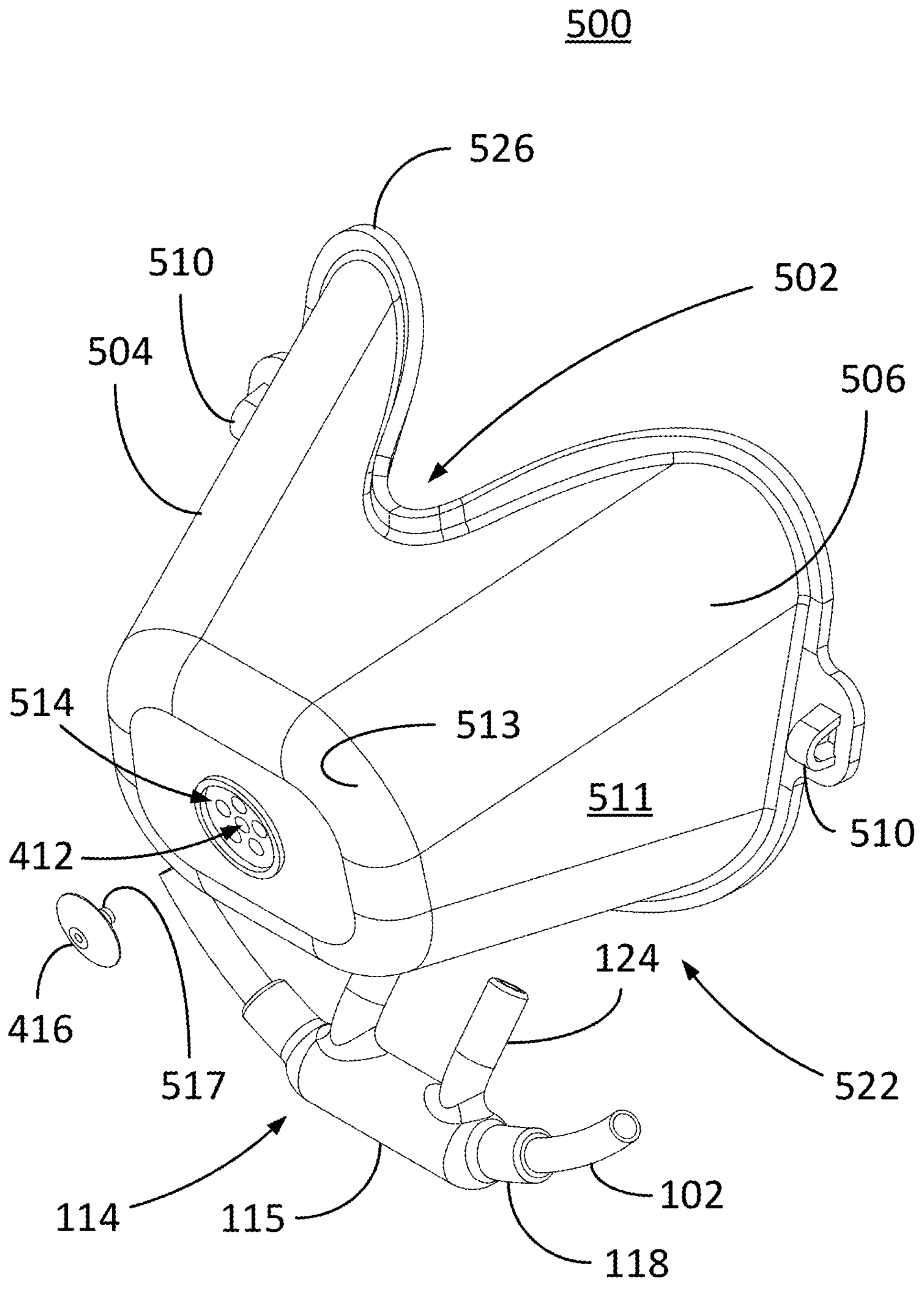

FIGS. 12A and 12B are line drawings of another low leakage nasal cannula embodiment consistent with embodiments of the present invention. FIG. 12A is three-quarter view line drawing of the low leakage nose cup/shielded nasal cannula embodiment 500, or simply "nose cup cannula 500". As shown, the cannula posts 124 extend into a cup configured to cover the majority of a person's nose 610 and nostrils 604. The nose cup cannula 500 generally comprises a nasal cannula 114 and a nose cup 506. As defined herein, the majority of a person's nose 610 is from their philtrum 615 to the bridge of their nose 606. The nose cup 506 comprises a perimeter 526 that covers the majority of a person's nose 610 to help shield oxygen 112 from flowing out of the cannula 114 into the external environment, which improves uptake of oxygen 112 into the wearer's nostrils 604. As shown in FIGS. 12A and 12B, the nose cup cannula 500 generally comprises a pair of cannula posts 124 extending orthogonally from a center cylinder 115. Each cannula post 124 terminates to an outlet port 110 at a post terminating end 125. Oxygen 112, from an oxygen source 130 as shown in FIG. 5A, flows through the oxygen tubes 102, into the nose cup cannula 500 and out through the outlet ports 110. The oxygen tubes 102 connect to intake tube sleeves 118 on either end 120 of the center cylinder 115.

The nose cup 506 is like a facemask that only covers (the majority of) a person's nose 610, which includes the tip of the nose 618, the sides of the nose 610 and at least half way up the bridge 606 of the wearer's nose 610. The nose bridge 606 is accommodated by the nose bridge 'cut-out' region 502. The cannula posts 124 penetrate into the nostrils 604. More specifically, oxygen 112 enters the nasal cavity via the cannula outlet ports 110. The nose cup 506 can be a soft pliable polymer, such as a flexible PVC, for example. The cannula posts 124 can be a relatively stiff polymer, such as a stiff PVC or some other suitable material. The nose cup 506 can be opaque or clear. The nose cup 506 comprises head-strap loops 510 on either side of the nose cup 506 that accommodate a head-strap that is configured to secure the nose cup 506 to a wearer's face 602.

FIG. 12B is an exploded offset angle view line drawing of the nose cup cannula embodiment 500 depicted in FIG. 12A. As shown, the nose cup cannula embodiment 500 generally comprises the cannula 114 of FIGS. 1A-3. Two cannula posts 124 extend from the center cylinder 115, each defining the outlet port 110 at the respective post terminating ends 125. As previously discussed, the intake tube sleeves 118 extend from the center cylinder 115. The nose cup cannula 500 comprises a center cylinder support 515 that is configured to retain the cannula 114 in place by locking around the center cylinder 115, as shown in FIG. 13B. The nose cup cannula 500 receives the cannula 114 at the bottom cup surface 522 of the nose cup 506. It should be appreciated that other cannula 114 connecting arrangements used with the nose cup cannula embodiment 500 would be readily apparent to those skilled in the art after seeing the present figures. The nose cup cannula 500 comprises a pair of post receiving apertures 544 (partially viewable in FIG. 13B) that are sized and configured to accommodate the cannula posts 124. The post receiving apertures 544 are oblong in shape to allow for some play to easily receive the cannula posts 124. In the center of the nose cup front face 508 of the nose cup 506 is a breathing port valve cover 416 that is attached via a center cover peg 417 cooperating with a cover peg hole 412. The nose cup front face 508 meets the nose cup sides 511 via the nose cup side-to-front interface 513. In this embodiment, there are five exhaust ports 414 the provide a passageway for exhalent to exit the nose cup 506. Hence, if a person breathes out through their nose 610, the pressure of from the person exhaling will open the breathing port valve cover 416 and the exhalent will exit the exhaust ports 414.

Figure 13A:
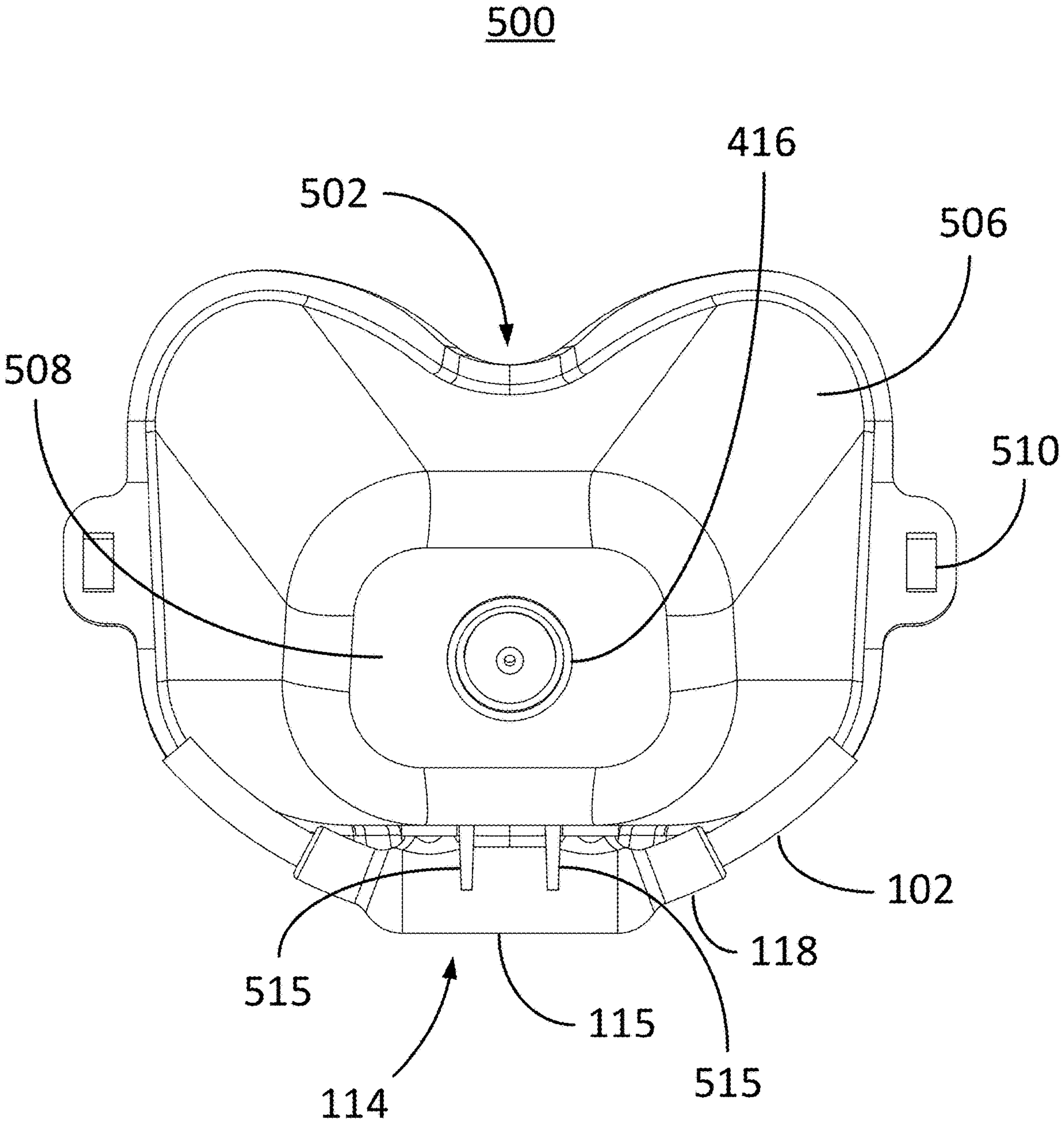
FIGS. 13A-13C are line drawings of various views of the nose cup cannula embodiment of FIGS. 12A and 12B consistent with embodiments of the present invention.
Figure 13B:
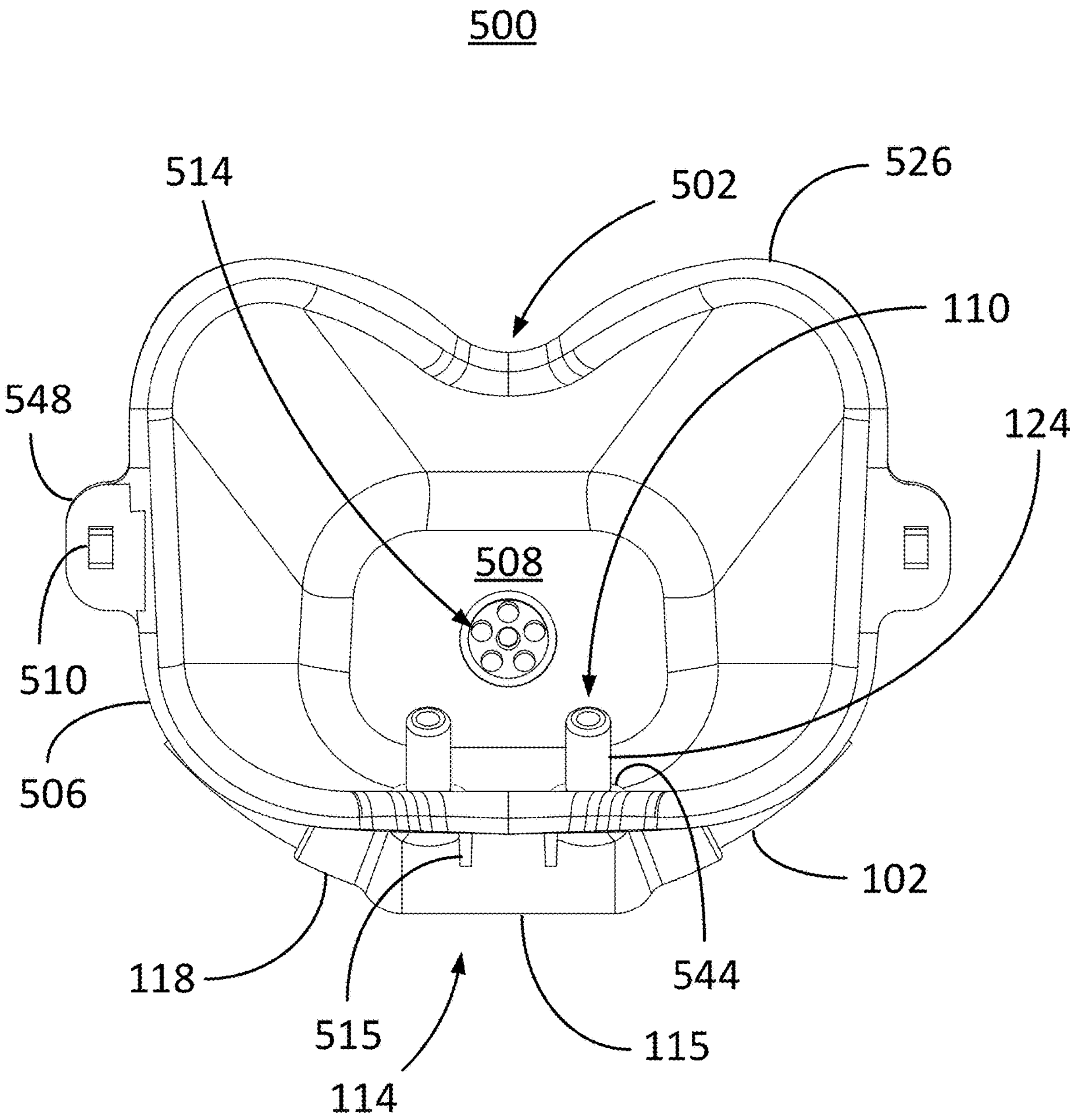
Figure 13C:
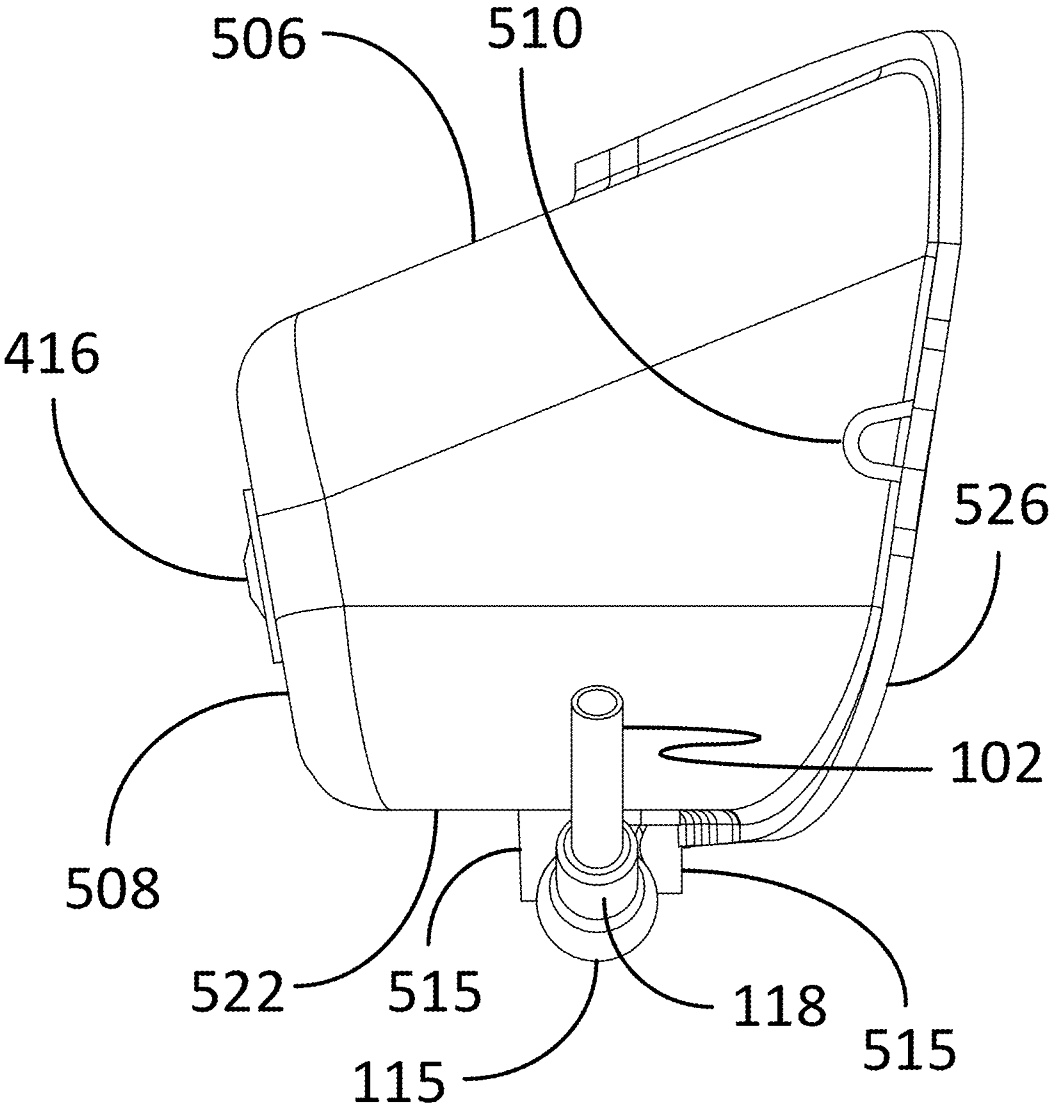

FIGS. 13A-13C are line drawings of various views of the nose cup cannula embodiment 500 consistent with embodiments of the present invention. FIG. 13A is a front view of the nose cup cannula 500 showing the cannula 114 connected to the bottom of the nose cup 506. The cannula 114 is connected to the nose cup 506 via retention clips 515 that lock around the center cylinder 115. The intake tube sleeves 118 and oxygen tubes 102 are shown here for reference. The breathing port valve cover 416 is depicted at the nose cup front face 508 of the nose cup 506. Also shown is the front view of the nose bridge region 502 and the head-strap loops 510.

FIG. 13B depicts a view looking into the nose cup 506 of the nose cup cannula embodiment 500 showing the cannula posts 124 extending up into the inner space of the nose cup 506 in a manner that the outlet ports 110 can blow oxygen 112 directly into a wearer's nostrils 604. The nose cup 506 accommodates the cannula posts 124 via the post receiving apertures 544. As shown in this angle, the cannula 114 is connected to the bottom of the nose cup 506 via retention clips 515 that lock around the other side of the center cylinder 115 from that shown in FIG. 13A. The intake tube sleeves 118 and oxygen tubes 102 are shown here for reference. The breathing port valve 514 is depicted at the inside surface of nose cup front face 508. Also shown is the back view of the nose bridge region 502 along the periphery 526 as well as the back sides of where the head-strap loops 510 are located (head-strap loop tabs 548).

FIG. 13C depicts a side view of the nose cup cannula embodiment 500 showing the width from the nose cup front face 508 to the cup periphery 526. From this perspective, the retention clips 515 are shown clamping around the center cylinder 115 at the bottom cup surface 522. The intake tube sleeves 118 and oxygen tubes 102 are shown here for reference. The breathing port valve cover 416 is in the middle of the nose cup front face 508, which will open should the wearer 600 exhale with sufficient force through their nose 610 to open the breathing port valve cover 416. Also from this angle, the head-strap loops 510 are prominently shown. As should be appreciated, the nose cup cannula embodiment 500 essentially encloses the nostrils 604 in the nose cup 506 thereby sealing off the nostrils 604 from an exterior environment to receive essentially the full slow of oxygen 112 into the nose 610.

FIG. 14 is a line drawing depicting a person's face 602 that is used to reference anatomy for embodiments of the present invention. The elements of interest of the person 600 are the face 602, the nose 610, the bridge of the nose 606, the philtrum 615, which is between the person's upper lip 620 and the bottom or underneath part of the nose 612. One of two nostrils 604 are located at the bottom part of the nose 612, which is shaded for reference. The nose bridge 606 (or the bridge of a person's nose 606) is also shaded for reference. The nose bridge 606 can extend above and below the shaded nose bridge region 606.

With the present description in mind, below are some examples of certain embodiments illustratively complementing some of the methods and apparatus embodiments FIG. 1A discussed above and presented in the figures to aid the reader. The elements called out below are provided by example to assist in the understanding of the present invention and should not be considered limiting. The reader will appreciate that the below elements and configurations can be interchangeable within the scope and spirit of the present invention.

In that light, one inventive aspect of the present invention is directed to a nasal cannula assembly 100, as shown in FIGS. 1A-3, that generally comprises a pair of cannula posts 124 extending from a center cylinder 115. Each of the cannula posts 124 defines an outlet port 110 at a post terminating end 125. A first intake tube sleeve 118A extends from a first center cylinder end 120A of the center cylinder 115 and a second intake tube sleeve 118B extends from a second center cylinder end 120B of the center cylinder 115. Each of the pair of nasal shields 106 having a convex curved outer surface 116 that is flush with said post terminating ends 125. A pair of nasal shields 106 are fixedly attached to the cannula posts 124 at the post terminating ends 125. The pair of nasal shields 106 each have a nasal shield aperture 108 that aligns with the outlet ports 110. The pair of nasal shields 106 are configured to essentially cover a pair of human nostrils 604.

The nasal cannula assembly embodiment 100 further envisions that each of the nasal shields 106 have an outward facing convex surface 116 defined as facing away from the center cylinder 115. The outward facing convex surfaces 116 are configured to interface the pair of human nostrils 604. This could further be wherein each of the pair of nasal shields 106 have an inward facing concave surface 116 defined as facing towards the center cylinder 115. It could optionally further be wherein each of the pair of nasal shields 106 defines a shield periphery 126. The pair of nasal shields 106 are configured to go into the human nostrils 604 up to the shield peripheries 126, wherein the shield peripheries 126 are not configured to go into the human nostrils 604.

The nasal cannula assembly embodiment 100 further imagining each of the intake tube sleeves 118A/118B being attached to an intake tube 102. This could further be wherein the cannula outlet ports 110 are in fluid communication with the intake tubes 102. Optionally, the intake tubes 102 can be in communication with an oxygen source 130. Fluid communication is defined herein as fluid flowing directly through and being in contact with the elements that are in communication or fluid communication.

The nasal cannula assembly embodiment 100 further envisioning the pair of nasal shields 106 being flexible. There could further be wherein the center cylinder 115, the cannula posts 124 and the intake tube sleeves 118 are rigid.

Another embodiment of the present invention envisions a nasal cannula 100 that generally comprises a center cylinder 115 defined between a first cylinder end 120A and a second cylinder end 120B with an oxygen input port 122 at the first cylinder end 120A, that is only one input port 122 to receive the oxygen 112. A pair of cannula posts 124 extend to post terminating ends 125 from said center cylinder 115 between said first and said second cylinder ends 120A and 120B, wherein each of said post terminating ends 125 comprising an outlet port 110. A pair of nasal shields 106 are each attached to one of said cannula posts 124. Each of said nasal shields 106 have a convex curved outer surface 116 with a shield aperture 108 extending therethrough. Each of said shield apertures 108 accommodate fluid communication between said oxygen input port 122 and said outlet ports 110.

The nasal cannula embodiment 100 is envisioned to further comprise a second oxygen input port 122B at the second cylinder end 120B.

The nasal cannula embodiment 100 further imagines the post terminating ends 125 being essentially flush with said convex curved outer surface 116.

The nasal cannula embodiment 100 further contemplates said pair of nasal shields 106 being configured to essentially cover a pair of human nostrils.

The nasal cannula embodiment 100 is envisioned to further comprise a first intake tube sleeve 118A extending from the first center cylinder end 120A and a second intake tube sleeve 118B extending from the second center cylinder end 120B.

The nasal cannula embodiment 100 further contemplates each of said nasal shields 106 having an inward facing concave surface 116 facing towards said center cylinder 115.

The nasal cannula embodiment 100 further envisions each of said nasal shields 106 comprising a shield periphery 126, wherein said nasal shields 106 are configured to go into said human nostrils up to said shield peripheries 126. The shield peripheries 126 are not configured to go into said human nostrils.

The nasal cannula embodiment 100 further imagines said pair of nasal shields 106 being flexible.

The nasal cannula embodiment 100 further considers each of said convex curved outer surfaces 116 being asymmetrical and wherein each of said shield apertures 108 is biased towards one side of said convex curved outer surfaces 116.

Yet another embodiment of the present invention envisions a flush shield nasal cannula 100 that comprises a center cylinder 115 that is defined between a first cylinder end 120A and a second cylinder end 120B, wherein the first cylinder end 120A is configured to receive oxygen 112. The flush shield nasal cannula 100 further comprises a pair of cannula posts 124 extending from said center cylinder 115 to outlet ports 110. A pair of asymmetrically shaped nasal shields 106 each attached to one of said cannula posts 124, wherein each of said nasal shields 106 comprises a convex curved outer surface 116 with a shield aperture 108 extending therethrough. Each of said shield apertures 108 accommodates fluid communication between said oxygen input port 122 and said outlet ports 110, wherein each of said convex curved outer surface 116 is configured to substantially block a wearer's nostril 604 from an exterior environment, that is not by way of through the nasal cannula 100. Optionally, it is further envisioned that each of said outlet ports 110 is defined by a distal rim 125 that does not extend beyond said convex curved outer surface 116.

Another embodiment of the present invention shown in FIGS. 4A-6 envision a concave cupped nasal cannula assembly 200 that generally comprises a pair of cannula posts 124 extending from a center cylinder 115. Each of the cannula posts 124 defines an outlet port 110 at a post terminating end 125. A first intake tube sleeve 118A extends from a first center cylinder end 120A of the center cylinder 115 and a second intake tube sleeve 118B extends from a second center cylinder end 120B of the center cylinder 115. A pair of outward facing cupped shaped nasal shields 206 are each fixedly attached to one of the cannula posts 124 with at least 20% of the cannula posts 124 extending distally beyond the pair of nasal shields 206. The pair of nasal shields 206 are configured to essentially cover a pair of human nostrils 604. By essentially, the nasal shields 206 cover at least 75% of the human nostrils 604 while preferred embodiments contemplate the nasal shields 206 covering more than 90% of the human nostrils 604.

The concave cupped nasal cannula assembly embodiment 200 further envisioning that each of the nasal shields 206 has a curved perimeter 226 that is not a closed loop. This could further be wherein less than 80% of each of the curved perimeter 226 is contiguous.

The concave cupped nasal cannula assembly embodiment 200 further envisions that each of the pair of nasal shields 206 is configured to essentially stay outside the human nostrils 604 when worn. A portion of the cannula posts 124 is configured to reside in the human nostrils 604 when worn.

The concave cupped nasal cannula assembly embodiment 200 further envisions each of the nasal shields 206 being integrated with a cannula post sleeve 204. Each of the cannula post sleeve 204 surrounds at least a portion of a corresponding one of the cannula posts 124.

The concave cupped nasal cannula assembly embodiment 200 further envisioning the cannula outlet ports 110 being in communication with the intake tubes 102.

The concave cupped nasal cannula assembly embodiment 200 further envisions the intake tubes 102 being in communication with an oxygen source 130.

The concave cupped nasal cannula assembly embodiment 200 further envisions the pair of nasal shields 106 being flexible. This could further be wherein the center cylinder 115, the cannula posts 124 and the intake tube sleeves 118 are rigid.

The concave cupped nasal cannula assembly embodiment 200 further envisioning that the nasal shields 206 are joined by a nasal shield joining bar 232 that spaces the nasal shields 206 at a same separation distance as the cannula posts 124.

Still another embodiment of the present invention contemplates a nasal plug cannula assembly 300 that comprises a pair of cannula posts 124 extending from a center cylinder 115, wherein each of the cannula posts 124 define an outlet port 110 at a post terminating end 125. A first intake tube sleeve 118A extends from a first center cylinder end 120A of the center cylinder 115 and a second intake tube sleeve 118B extends from a second center cylinder end 120B of the center cylinder 115. A pair of compressible nose plugs 306 that are each fixedly attached to one of the cannula posts 124 are configured to essentially block a pair of human nostrils 604.

The nasal plug cannula assembly 300 further envisioning each of the compressible nose plugs 306 being composed of foam.

The nasal plug cannula assembly 300 envisions that each of the compressible nose plugs 306 are cylindrical and surround the cannula posts 124 for at least 60% of a cannula post length of the cannula posts 124. This can further be wherein the nose plugs 306 extends beyond the cannula posts 124 up to +/−10% of the cannula post length.

The nasal plug cannula assembly 300 further imagines the compressible nose plugs 306 being configured to be compressed prior to inserting them into the human nostrils 604 and being configured to expand inside of the human nostrils 604 thereby blocking the human nostrils 604.

The nasal plug cannula assembly 300 envisions that the cannula outlet ports 110 are in communication with the intake tubes 102.

The nasal plug cannula assembly 300 envisions that the intake tubes 102 are in communication with an oxygen source 130.

The nasal plug cannula assembly 300 envisions that center cylinder 115, the cannula posts 124 and the intake tube sleeves 118 are flexible.

The nasal plug cannula assembly 300 envisions that at least a portion of each of the compressible nose plugs 306 are configured to essentially penetrate into the human nostrils 604 when worn.

The nasal plug cannula assembly 300 envisions that the cannula posts 124 are essentially flush with terminal ends 317 of the compressible nose plugs 306.

In yet another embodiment of the present invention a nasal cup cannula 400, as shown in FIGS. 10A-11D, is envisioned comprising a pair of cannula posts 124 extending from a center cylinder 115, wherein each of the cannula posts 124 define an outlet port 110 at a post terminating end 125. A first intake tube sleeve 118A extends from a first center cylinder end 120A of the center cylinder 115 and a second intake tube sleeve 118B extends from a second center cylinder end 120B of the center cylinder 115. A nasal cup 406, which is defined by a cup perimeter 426, is configured to cover a person's nostrils 604 and between 50% and 100% of a bottom of the person's nose 612. A portion of the nasal cup 406 is configured to interface the person's philtrum 615. A pair of cannula post apertures 444 are located in the nasal cup 406 at a base side 408 of the nasal cup 406. Each of the cannula posts 124 penetrate through a corresponding one of the cannula post apertures 444. The post terminating ends 125 extend beyond the nasal cup periphery 426.

As further shown in FIG. 11A, the nasal cup cannula 400 further envisions the nasal cup periphery 426 comprising a nose periphery 466 and a philtrum periphery 468. A front side 460, a first end side 462 and a second end side 464 all extend from the base side 408 to the nose periphery 466. The philtrum periphery 427 is defined where the first end side 462, the second end side 464 and the base side 408 terminate. The front side 460, the first end side 462, the second end side 464 and the base side 408 form a three-quarter box. The nose periphery 466 is configured to interface the bottom of the person's nose 612 and the philtrum periphery 427 is configured to interface the person's philtrum 615.

The nasal cup cannula 400 can further comprise a lower center cylinder support 410 that extends from the base side 408 and around a portion of a circumference of the center cylinder 115. This can further be where at least one upper center cylinder support 425 that cooperates with the lower center cylinder support 410, both the at least one upper center cylinder support 425 and the lower center cylinder support 410 collectively surrounds the portion of the circumference of the center cylinder 115, the center cylinder 115 is retained on the nasal cup 406 via the at least one upper center cylinder support 425 and the lower center cylinder support 410.

The nasal cup cannula 400 can further comprise an exhaust port hub 422 that has at least one exhaust port 414, wherein the exhaust port hub 422 is in the base side 408 and the at least one exhaust port 414 is a channel that penetrates through the base side 408. This embodiment can further comprise a breathing port valve cover 416 that covers and blocks off the channel in the at least one exhaust port 414 unless there is a positive pressure that exceeds a predetermined threshold in the at least one exhaust port 414.

The nasal cup cannula 400 is further envisioned to be configured to extend over a front of a person's nose 618 (nose tip).

Still, yet another embodiment of the present invention contemplates a nose cup cannula 500 that generally comprises a pair of cannula posts 124 that extend from a center cylinder 115, wherein each of the cannula posts 124 define an outlet port 110 at a post terminating end 125. A first intake tube sleeve 118A extends from a first center cylinder end 120A of the center cylinder 115 and a second intake tube sleeve 118B extends from a second center cylinder end 120B of the center cylinder 115. A nose cup 506 defined by a cup perimeter 526 that is configured to cover a person's nose 610 up to at least along a nose bridge 606 of the person's nose 610. The nose cup 506 is configured to seal against a person's face 602 and the nose bridge 606. A pair of cannula post apertures 544 penetrate in through the nose cup 506 at a base side 522 of the nose cup 506 of the nose cup 506. Each of the cannula posts 124 penetrate through a corresponding one of the cannula post apertures 544. A pair of head-strap loops 510 are on either side of the nose cup 506 and are configured to retain a head-strap (not shown). The head-strap configured to secure the nose cup cannula 500 against the person's face 602 and the nose bridge 606.

As shown in FIG. 14B, the nose cup cannula 500 can further be where the cup periphery 526 extends on either side of the person's nose on the person's face, around a person's philtrum 615 and across the nose bridge 606.

The nose cup cannula 500 can further comprise at least one lower center cylinder support 515 and at least one upper center support 515 that extends from the base side 522 of the nose cup 506 and surrounds a portion of a circumference of the center cylinder 115. The center cylinder 115 is retained on the nose cup 506 via the center supports 515.

The nose cup cannula 500 can further comprise an exhaust port hub 422 that has at least one exhaust port 414 wherein the exhaust port hub 422 is in front side 508 of the nose cup 506. The at least one exhaust port 414 is a channel that penetrates through the front side 508. This embodiment can further comprise a breathing port valve cover 416 that covers and blocks off the channel in the at least one exhaust port 414 unless there is a positive pressure that exceeds a predetermined threshold in the at least one exhaust port 414 (meaning the valve opens when a person wearing the nose cup cannula 500 exhales with enough force to open the valve cover 416).

The above embodiments are not intended to be limiting to the scope of the invention whatsoever because many more embodiments are easily conceived within the teachings and scope of the instant description. Moreover, the corresponding elements in the above example should not be considered limiting.

It is to be understood that even though numerous characteristics and advantages of various embodiments of the present invention have been set forth in the foregoing description, together with the details of the structure and function of various embodiments of the invention, this disclosure is illustrative only, and changes may be made in detail, especially in matters of structure and arrangement of parts within the principles of the present invention to the full extent indicated by the broad general meaning of the terms used herein. For example, though embodiments of the present invention describe variations for cannulas that block a nostril or cover nostrils, certain inventive elements can be equally applied to other kinds of arrangements without departing from the scope and spirit of the present invention. It should also be appreciated that the appropriate mechanical components not discussed in detail in the present disclosure must be implemented in accordance known to those skilled in the art. It should be appreciated that elements of various embodiments described herein can be combined in obvious manners by a person skilled in the art that understands the content of the present specification without departing from the scope of the subject matter presented herein. Further, the term "one" is synonymous with "a", which may be a first of a plurality.

It will be clear that the present invention is well adapted to attain the ends and advantages mentioned as well as those inherent therein. While presently preferred embodiments have been described for purposes of this disclosure, numerous changes may be made which readily suggest themselves to those skilled in the art and which are encompassed in the appended claims.

What is claimed is:

1. A nasal cannula assembly comprising:

a pair of cannula posts extending from a center cylinder, wherein each of the cannula posts is a cylindrical tube having a single inner diameter and a single outer diameter and defines an outlet port at a post terminating end;

a first intake tube sleeve extending from a first center cylinder end of the center cylinder and a second intake tube sleeve extending from a second center cylinder end of the center cylinder; and a pair of nasal shield units each consisting of a uniform cylindrical shaped cannula post sleeve that extends from a proximal post sleeve end to an umbrella shaped nasal shield defined by a convex outer surface and a concave inner surface, the convex outer surface comprising a progressively increasing diameter starting at a shield apex and ending at a peripheral edge, each of the uniform cylindrical shaped cannula post sleeves slidingly engaged over a corresponding one of the cannula posts, wherein each of the shield apexes is flush with the post terminating ends, each of the shield apexes comprises a nasal shield aperture that aligns with the outlet ports, the pair of umbrella shaped nasal shields configured to essentially cover a pair of human nostrils.

2. The nasal cannula assembly of claim 1 further comprising an angle defined from the peripheral edge along the convex curved outer surface of each of the nasal shield units that is less than sixty-five degrees.

3. The nasal cannula assembly of claim 1, wherein each of the pair of nasal shield units are pliable.

4. The nasal cannula assembly of claim 1, wherein only a portion of the pair of shield units are configured to go into the human nostrils with the peripheral edges are not configured to go into the human nostrils.

5. The nasal cannula assembly of claim 1, wherein each of the uniform cylindrical shaped cannula post sleeves is fixedly attached to the corresponding one of the cannula posts.

6. The nasal cannula assembly of claim 5, wherein the outlet ports are in fluid communication with the intake tubes.

7. The nasal cannula assembly of claim 5, wherein the intake tubes are in communication with an oxygen source.

8. The nasal cannula assembly of claim 1, wherein the pair of nasal shields are composed of either rubber or latex.

9. The nasal cannula assembly of claim 8, wherein the center cylinder, the cannula posts and the intake tube sleeves are of a rigid unitary formation, wherein the intake tube sleeves comprise an intake tube diameter that is smaller than a central cylinder diameter of the central cylinder.

10. A nasal cannula comprising:

a center cylinder defined between a first cylinder end and a second cylinder end, an oxygen input port at the first cylinder end;

a pair of cylindrical cannula posts extending to post terminating ends from the center cylinder between the first and the second cylinder ends, each of the post terminating ends comprising an outlet port, each of the cylindrical cannula posts consists of a single inner diameter and a single outer diameter;

a pair of nasal shield units each consisting of a uniform cylindrical shaped cannula post sleeve that extends from a proximal post sleeve end to an umbrella shaped nasal shield defined by a convex outer surface and a concave inner surface, the convex outer surface comprising a progressively increasing diameter starting at a shield apex and ending at a peripheral edge, each of the uniform cylindrical shaped cannula post sleeves slidingly engaged over a corresponding one of the cannula posts, each of the shield apexes comprise an aperture that align with the outlet ports, each of the shield apex is flush with the post terminating ends.

11. The nasal cannula of claim 10 further comprising a second oxygen input port at the second cylinder end.

12. The nasal cannula of claim 10 further comprising an angle defined from the peripheral edge along the convex curved outer surface of each of the nasal shield units that is less than sixty-five degrees, the peripheral edge is devoid of a chamfer.

13. The nasal cannula of claim 10, wherein the pair of nasal shields are configured to essentially cover a pair of human nostrils.

14. The nasal cannula of claim 10 further comprising a first intake tube sleeve extending from the first center cylinder end and a second intake tube sleeve extending from the second center cylinder end, wherein the first and the second intake tube sleeves comprise an intake tube diameter that is smaller than a central cylinder diameter of the central cylinder.

15. The nasal cannula of claim 10, wherein the concave inner surfaces face towards the center cylinder.

16. The nasal cannula of claim 10, wherein a portion of the umbrella shaped nasal shields are configured to go into the human nostrils, the portion does not include the peripheral edge.

17. The nasal cannula of claim 10, wherein each of the umbrella shaped nasal shields defines a first distance extending from the shield apex to the peripheral edge closest to an adjacent one of the umbrella shaped nasal shields and a second distance extending from the shield apex to the peripheral edge in the opposite direction, the first distance is shorter than the second distance.

18. The nasal cannula of claim 17, wherein each of the umbrella shaped nasal shields defines a third distance extending from the shield apex to the peripheral edge at a front end of the nasal cannula and a fourth distance extending from the shield apex to the peripheral edge at a front end of the nasal cannula, the third distance is shorter than the fourth distance, the front end is configured to point away from a wearer of the nasal cannula and the rear end is configured to point towards the wearer of the nasal cannula.

19. A flush shield nasal cannula comprising:

a center cylinder defined between a first cylinder end and a second cylinder end that is configured to receive oxygen;

a pair of cannula posts extending from the center cylinder to outlet ports, wherein each of the cylindrical cannula posts are defined by a single inner diameter and a single outer diameter;

a pair of nasal shield units, each comprising a cylindrical cannula post sleeve of uniform diameter and an umbrella-shaped nasal shield, the cylindrical cannula post sleeve extending from a proximal sleeve end to the umbrella-shaped nasal shield, the umbrella-shaped nasal shield defined by a convex outer surface and a concave inner surface, the convex outer surface extending from a shield apex to a peripheral edge with a progressively increasing diameter;

each of the cannula posts are essentially encapsulated by a corresponding one of the cylindrical cannula post sleeves wherein the outlet port aligns with an aperture at the shield apex, each of the post terminating ends is flush with the corresponding shield apex.

20. The flush shield nasal cannula of claim 19, wherein each of the umbrella shaped nasal shields defines a first distance defined as extending from the shield apex to the peripheral edge closest to an adjacent one of the umbrella shaped nasal shields, a second distance extending from the shield apex to the peripheral edge in the opposite direction, the first distance is shorter than the second distance, a third distance extending from the shield apex to the peripheral edge at a front end of the nasal cannula and a fourth distance extending from the shield apex to the peripheral edge at a front end of the nasal cannula, the third distance is shorter than the fourth distance, the front end is configured to point away from a wearer of the nasal cannula and the rear end is configured to point towards the wearer of the nasal cannula.

* * * * *